United States Patent
Gnanashanmugam et al.

(10) Patent No.: US 9,028,391 B2
(45) Date of Patent: *May 12, 2015

(54) APPARATUS AND METHODS FOR TREATING PULMONARY HYPERTENSION

(71) Applicant: The Board of Trustees of the Leland Stanford Junior University, Palo Alto, CA (US)

(72) Inventors: Swaminadhan Gnanashanmugam, San Francisco, CA (US); Jonathan A. Coe, Menlo Park, CA (US); Insoo Suh, San Francisco, CA (US); Jeremy Christopher Koehler, East Palo Alto, CA (US)

(73) Assignee: The Board of Trustees of the Leland Stanford Jr. University, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/244,900

(22) Filed: Apr. 4, 2014

(65) Prior Publication Data

US 2014/0221975 A1  Aug. 7, 2014

Related U.S. Application Data

(63) Continuation of application No. 13/715,944, filed on Dec. 14, 2012.

(60) Provisional application No. 61/576,318, filed on Dec. 15, 2011.

(51) Int. Cl.
*A61N 1/36* (2006.01)
*A61N 1/05* (2006.01)
(Continued)

(52) U.S. Cl.
CPC .......... *A61N 1/36117* (2013.01); *A61N 1/0551* (2013.01); *A61M 25/10* (2013.01);
(Continued)

(58) Field of Classification Search
CPC .................. A61B 2018/0016; A61B 2018/00214–2018/00267; A61N 1/0448; A61N 1/0551; A61N 1/3605; A61N 1/36114; A61N 1/36117; A61N 2005/0602; A61N 2007/003
USPC ...................... 600/20–34, 45, 48–50; 607/44; 606/20–34, 45, 48–50
See application file for complete search history.

(56) References Cited

U.S. PATENT DOCUMENTS 6,292,695 B1  9/2001  Webster et al.
6,411,852 B1  6/2002  Danek et al.
(Continued)

FOREIGN PATENT DOCUMENTS

AU  2007290727 B2  1/2012
EP  1637086 A1  3/2006
(Continued)

OTHER PUBLICATIONS

Chinese Clinical Trial Register (ChiCTR): "Pulmonary Artery Denervation in Patients with Pulmonary Artery Hypertention (The PADN-2 trial): a randomised controlled trial" dated Apr. 12, 2012, http://www.chictr.org/en/proj/show.aspx?proj=2756, printed Apr. 28, 2014 (4 pages).

(Continued)

*Primary Examiner* — Charles A Marmor, II
*Assistant Examiner* — Carrie R Dorna
(74) *Attorney, Agent, or Firm* — William A. English; Vista IP Law Group LLP

(57) ABSTRACT

A method is described for decreasing activity of at least one sympathetic nerve, nerve fiber or neuron innervating at least one blood vessel in the pulmonary vasculature of a patient to ameliorate pulmonary hypertension. In one embodiment, the method may involve advancing an intravascular treatment device to a target location in a target blood vessel within the pulmonary vasculature of the patient and using the treatment device to decrease activity of at least one sympathetic nerve, nerve fiber or neuron innervating the target blood vessel at or near the target location to ameliorate pulmonary hypertension.

15 Claims, 26 Drawing Sheets

(51) Int. Cl.

| | | |
|---|---|---|
| *A61B 17/00* | (2006.01) | |
| *A61B 18/02* | (2006.01) | |
| *A61B 18/04* | (2006.01) | |
| *A61B 18/18* | (2006.01) | |
| *A61M 25/00* | (2006.01) | |
| *A61N 2/02* | (2006.01) | |
| *A61N 2/06* | (2006.01) | |
| *A61N 5/10* | (2006.01) | |
| *A61B 18/14* | (2006.01) | |
| *A61M 25/10* | (2013.01) | |
| *A61M 29/00* | (2006.01) | |
| *A61N 7/02* | (2006.01) | |
| *A61N 7/00* | (2006.01) | |
| *A61M 29/02* | (2006.01) | |
| *A61B 18/00* | (2006.01) | |

(52) U.S. Cl.
CPC ............... *A61B 17/00* (2013.01); *A61B 18/02* (2013.01); *A61B 18/04* (2013.01); *A61B 18/18* (2013.01); *A61B 18/1815* (2013.01); *A61M 25/00* (2013.01); *A61M 29/00* (2013.01); *A61N 2/02* (2013.01); *A61N 2/06* (2013.01); *A61N 5/1002* (2013.01); *A61N 7/022* (2013.01); *A61N 2007/003* (2013.01); *A61M 25/1002* (2013.01); *A61M 29/02* (2013.01); *A61B 18/1492* (2013.01); *A61B 2018/0022* (2013.01); *A61B 2018/00375* (2013.01); *A61B 2018/00434* (2013.01); *A61B 2018/00577* (2013.01); *A61B 2018/0212* (2013.01); *A61B 2018/143* (2013.01); *A61B 2018/1432* (2013.01); *A61B 2018/00357* (2013.01); *A61B 2018/00613* (2013.01); *A61B 2018/00345* (2013.01); *A61M 25/0043* (2013.01); *A61M 2025/006* (2013.01)

(56) References Cited

U.S. PATENT DOCUMENTS

| | | | |
|---|---|---|---|
| 6,493,589 | B1 | 12/2002 | Medhkour et al. |
| 6,564,096 | B2 | 5/2003 | Mest |
| 6,690,971 | B2 | 2/2004 | Schauerte et al. |
| 7,260,431 | B2 | 8/2007 | Libbus et al. |
| 7,269,457 | B2 | 9/2007 | Shafer et al. |
| 7,363,076 | B2 | 4/2008 | Yun et al. |
| 7,367,951 | B2 | 5/2008 | Bennett et al. |
| 7,587,238 | B2 | 9/2009 | Moffitt et al. |
| 7,616,990 | B2 | 11/2009 | Chavan et al. |
| 7,623,926 | B2 | 11/2009 | Rossing et al. |
| 7,630,760 | B2 | 12/2009 | Libbus et al. |
| 7,664,548 | B2 | 2/2010 | Amurthur et al. |
| 7,711,430 | B2 | 5/2010 | Errico |
| 7,715,915 | B1 | 5/2010 | Ryu et al. |
| 7,734,355 | B2 | 6/2010 | Cohen et al. |
| 7,744,618 | B2 | 6/2010 | Shuros et al. |
| 7,783,353 | B2 | 8/2010 | Libbus et al. |
| 7,801,604 | B2 | 9/2010 | Brockway et al. |
| 7,826,899 | B1 | 11/2010 | Ryu et al. |
| 7,828,795 | B2 | 11/2010 | Privitera et al. |
| 7,899,527 | B2 | 3/2011 | Yun et al. |
| 7,925,342 | B2 | 4/2011 | Amurthur et al. |
| 7,937,147 | B2 | 5/2011 | Sih et al. |
| 8,019,435 | B2 | 9/2011 | Hastings et al. |
| 8,027,724 | B2 | 9/2011 | Wei et al. |
| 8,052,668 | B2 | 11/2011 | Sih |
| 8,073,538 | B2 | 12/2011 | Peters et al. |
| 8,088,127 | B2 | 1/2012 | Mayse et al. |
| 8,249,705 | B1 | 8/2012 | Kieval et al. |
| 2005/0261672 | A1 | 11/2005 | Deem et al. |
| 2005/0283148 | A1 | 12/2005 | Janssen et al. |
| 2006/0116737 | A1 | 6/2006 | Libbus |
| 2006/0167498 | A1 | 7/2006 | DiLorenzo |
| 2006/0217772 | A1 | 9/2006 | Libbus et al. |
| 2007/0129720 | A1 | 6/2007 | Demarais et al. |
| 2007/0129760 | A1 | 6/2007 | Demarais et al. |
| 2007/0142879 | A1 | 6/2007 | Greenberg et al. |
| 2007/0191904 | A1* | 8/2007 | Libbus et al. .................. 607/44 |
| 2007/0255379 | A1 | 11/2007 | Williams et al. |
| 2008/0255642 | A1 | 10/2008 | Zarins et al. |
| 2008/0306570 | A1 | 12/2008 | Rezai et al. |
| 2009/0024124 | A1 | 1/2009 | Lefler et al. |
| 2009/0062873 | A1 | 3/2009 | Wu et al. |
| 2009/0118780 | A1 | 5/2009 | DiLorenzo |
| 2009/0216290 | A1 | 8/2009 | Ruse et al. |
| 2009/0254142 | A1 | 10/2009 | Edwards et al. |
| 2010/0094196 | A1 | 4/2010 | Nash et al. |
| 2010/0113928 | A1 | 5/2010 | Thapliyal et al. |
| 2010/0114095 | A1 | 5/2010 | Janssen et al. |
| 2010/0137860 | A1 | 6/2010 | Demarais et al. |
| 2010/0217347 | A1 | 8/2010 | Swoyer et al. |
| 2010/0228317 | A1 | 9/2010 | Libbus et al. |
| 2010/0241188 | A1 | 9/2010 | Errico et al. |
| 2010/0249773 | A1 | 9/2010 | Clark et al. |
| 2010/0249859 | A1 | 9/2010 | DiLorenzo |
| 2010/0268307 | A1 | 10/2010 | Demarais et al. |
| 2010/0274221 | A1 | 10/2010 | Sigg et al. |
| 2010/0286684 | A1 | 11/2010 | Hata et al. |
| 2010/0286734 | A1 | 11/2010 | Yun et al. |
| 2010/0298905 | A1 | 11/2010 | Simon |
| 2011/0118725 | A1 | 5/2011 | Mayse et al. |
| 2011/0152855 | A1 | 6/2011 | Mayse et al. |
| 2011/0178569 | A1 | 7/2011 | Parnis et al. |
| 2011/0202098 | A1 | 8/2011 | Demarais et al. |
| 2011/0207758 | A1 | 8/2011 | Sobotka et al. |
| 2011/0257708 | A1 | 10/2011 | Kramer et al. |
| 2011/0276103 | A1 | 11/2011 | Maile et al. |
| 2011/0301587 | A1 | 12/2011 | Deem et al. |
| 2011/0301679 | A1 | 12/2011 | Rezai et al. |
| 2012/0029505 | A1 | 2/2012 | Jenson |
| 2012/0029509 | A1 | 2/2012 | Smith |
| 2012/0029510 | A1 | 2/2012 | Haverkost |
| 2012/0029511 | A1 | 2/2012 | Smith et al. |
| 2012/0029512 | A1 | 2/2012 | Willard et al. |
| 2012/0065554 | A1 | 3/2012 | Pikus |
| 2012/0123258 | A1 | 5/2012 | Willard |
| 2012/0123406 | A1 | 5/2012 | Edmunds et al. |
| 2012/0143294 | A1 | 6/2012 | Clark et al. |
| 2012/0157992 | A1 | 6/2012 | Smith et al. |
| 2012/0157993 | A1 | 6/2012 | Jenson et al. |
| 2012/0158104 | A1 | 6/2012 | Huynh et al. |
| 2012/0165815 | A1 | 6/2012 | Collins et al. |
| 2012/0172680 | A1 | 7/2012 | Gelfand et al. |
| 2012/0172870 | A1 | 7/2012 | Jenson et al. |
| 2012/0184952 | A1 | 7/2012 | Jenson et al. |
| 2012/0232551 | A1 | 9/2012 | Swanson et al. |
| 2012/0277839 | A1 | 11/2012 | Kramer et al. |
| 2012/0290024 | A1 | 11/2012 | Zhang et al. |
| 2012/0294424 | A1 | 11/2012 | Chin et al. |
| 2012/0302909 | A1 | 11/2012 | Mayse et al. |

FOREIGN PATENT DOCUMENTS

| | | |
|---|---|---|
| RU | 95108755 A1 | 2/1997 |
| RU | 2074645 C1 | 3/1997 |
| WO | WO 9301862 A1 | 2/1993 |
| WO | WO 9965561 A1 | 12/1999 |
| WO | WO 2010110785 A1 | 9/2010 |
| WO | WO 2011075328 A1 | 6/2011 |
| WO | WO 2011091069 A1 | 7/2011 |
| WO | WO 2012068268 A2 | 5/2012 |
| WO | WO 2012120495 A1 | 9/2012 |
| WO | WO 2012149341 A1 | 11/2012 |
| WO | WO 2012149511 A2 | 11/2012 |
| WO | WO 2012154800 A1 | 11/2012 |

OTHER PUBLICATIONS

Chinese Clinical Trial Register (ChiCTR): "First-in-Man of Pulmonary artery denervation for treatment of pulmonary artery hypertension: the PADN-1 trial" dated Apr. 6, 2012, http://www.chictr.org/en/proj/show.aspx?proj=2741, printed Apr. 28, 2014 (3 pages).
Chinese Clinical Trial Register (ChiCTR): "Percutaneous pulmonary arterial denervation for treatment of chronic heart failure with sec-

(56) References Cited

OTHER PUBLICATIONS ondary pulmonary hypertension" dated Nov. 2, 2012, http://www.chictr.org/en/proj/show.aspx?proj=3677, printed Apr. 28, 2014 (3 pages).

Flues et al, "Cardiac and pulmonary arterial remodeling after sinoaortic denervation in normotensive rats", dated Jan. 26, 2012, http://www.ncbi.nlm.nih.gov/pubmed/22079748, printed Apr. 28, 2014 (2 pages).

Naeije et al., "Pulmonary vascular responses to surgical chemodenervation and chemical sympathectomy in dogs", dated Jan. 1989, http://www.ncbi.nlm.nih.gov/pubmed/2917946, printed Apr. 28, 2012 (2 pages).

* cited by examiner

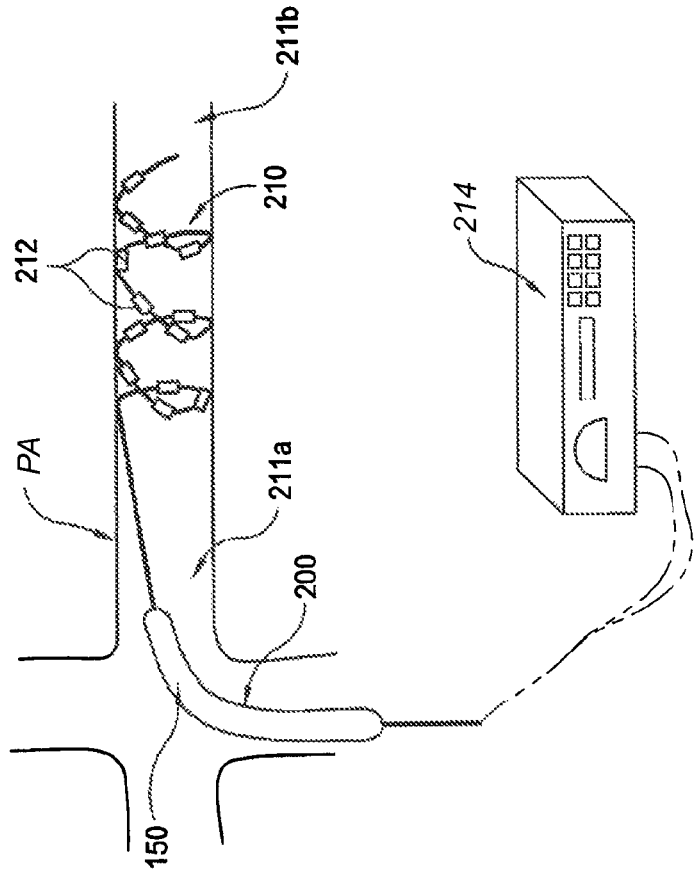
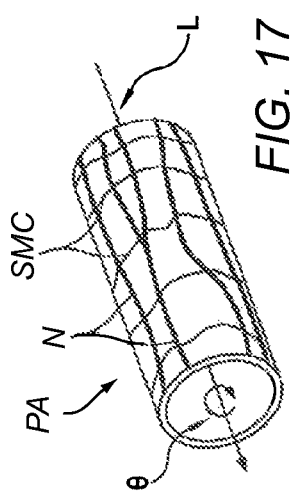
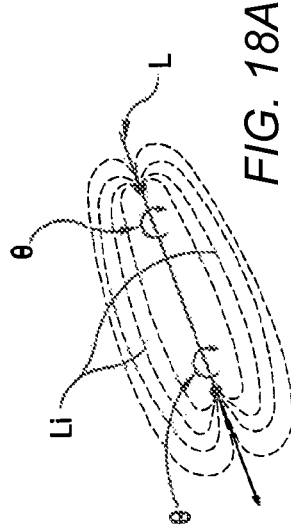

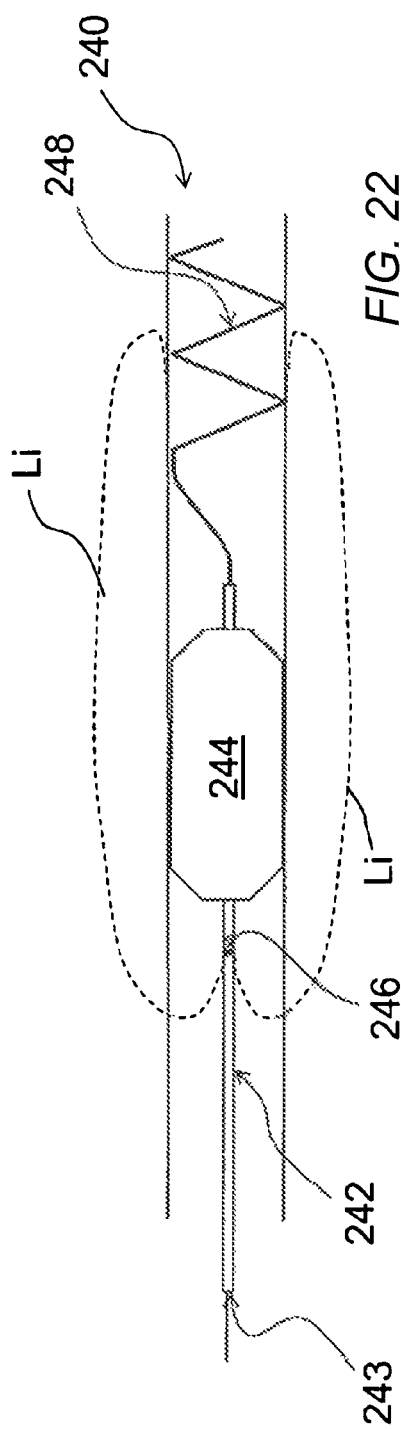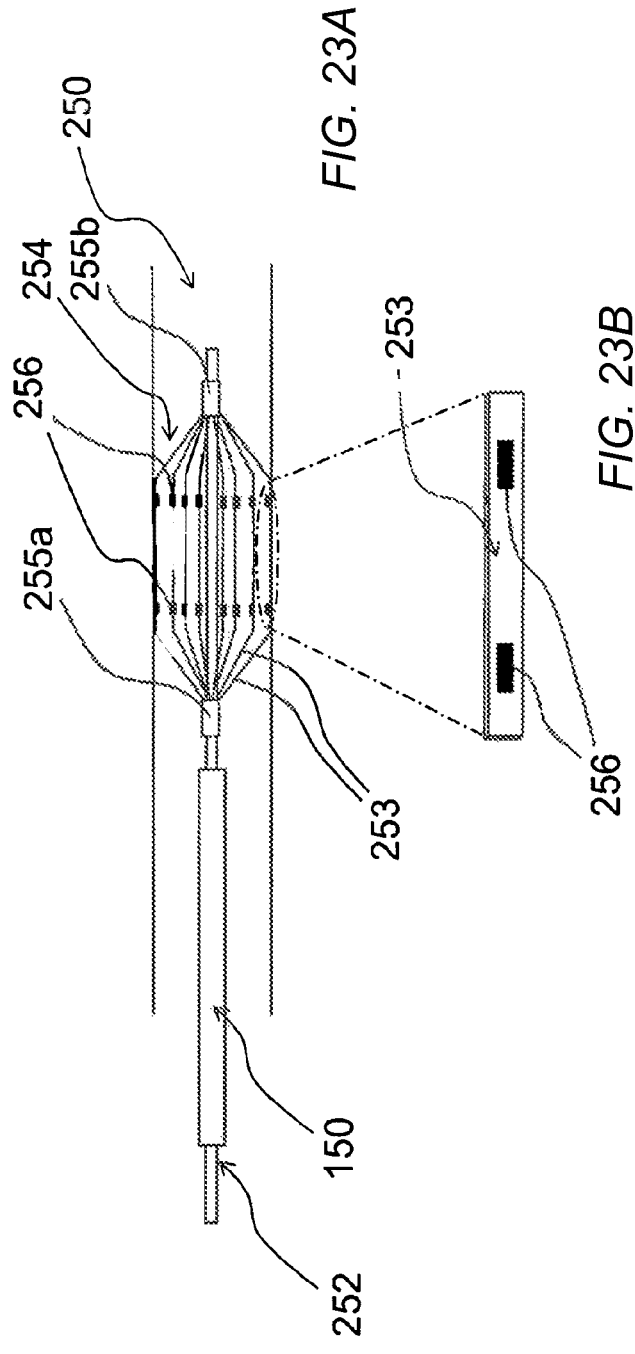

APPARATUS AND METHODS FOR TREATING PULMONARY HYPERTENSION

CROSS REFERENCE TO RELATED APPLICATIONS

This application is a continuation of co-pending application Ser. No. 13/715,944, filed Dec. 14, 2012, which claims priority to U.S. Provisional Patent Application Ser. No. 61/576,318, filed Dec. 15, 2011, and entitled, "Method for Treating Pulmonary Hypertension," the entire disclosure of which are incorporated by reference herein.

TECHNICAL FIELD

The present application is directed generally to medical devices, systems and methods. More specifically, the application is directed to devices, systems and methods for treating one or more nerves, nerve fibers or neurons to treat pulmonary hypertension and/or other pulmonary vascular disorders.

The present application is directed generally to medical devices, systems and methods. More specifically, the application is directed to devices, systems and methods for treating one or more nerves, nerve fibers or neurons to treat pulmonary hypertension and/or other pulmonary vascular disorders.

BACKGROUND

Pulmonary hypertension is a disease phenomenon of multifactorial etiology with high morbidity and mortality. The disease causes increased work for the right side of the heart and eventually hypertrophy and dysfunction of not only the right side of the heart, but often the left side as well. The prognosis of pulmonary hypertension historically has been poor, with median survival historically being around 2.8 years. Currently, with the advent of new pharmacologic therapies, survival has improved to 50 to 60% at 5 years. However, many patients continue to progress to worsening stages of pulmonary hypertension, and despite improvements in therapy, prognosis for the condition remains grave. Furthermore, pharmacological agents are the only currently available treatment for pulmonary hypertension, and they are extremely expensive (as much as $100,000 per year for an adult) and still not entirely efficacious.

Therefore, it is desirable to have new treatments for pulmonary hypertension. Ideally, such treatments would be minimally invasive. Also ideally, such treatments would reduce or negate the need for expensive pharmaceutical remedies and would be permanent or at least long lasting. At least some of these objectives may be met by the embodiments described below.

BRIEF SUMMARY

In one aspect, a method of decreasing activity of at least one sympathetic nerve, nerve fiber or neuron innervating at least one blood vessel in the pulmonary vasculature of a patient to ameliorate pulmonary hypertension may involve: advancing an intravascular treatment device to a target location in a target blood vessel within the pulmonary vasculature of the patient; and using the treatment device to decrease activity of at least one sympathetic nerve, nerve fiber or neuron innervating the target blood vessel at or near the target location to ameliorate pulmonary hypertension.

In some embodiments, advancing the treatment device may involve advancing an energy transmission device that emits energy such as, but not limited to, monopolar radiofrequency, bipolar radiofrequency, other forms of radiofrequency, high intensity focused ultrasound, low frequency ultrasound, other forms of ultrasound, microwave, light, heat, cold radiation, phototherapy, magnetic, electrical, electromagnetic, cryotherapy, plasma, mechanical, chemical, kinetic, potential, nuclear, elastic and/or hydrodynamic energy. In such embodiments, using the treatment device typically involves emitting energy from the catheter.

In some embodiments, advancing the treatment device may involve advancing a substance emitting catheter, and using the treatment device may involve emitting a substance from the catheter. For example, the emitted substance may include, but is not limited to, saline, phenol, ethanol, vincristine, an antineoplastic drug, botulinum toxin, other neurotoxins, anesthetic agents, including but not limited to depolarizing, non-depolarizing agents, such as Marcaine® (generic bupivacaine), lidocaine, or other anesthetic agents, and/or other agents capable of reducing nerve signal transmission. Optionally, the method may further include, before emitting the substance, advancing at least one substance delivery member out of the catheter, where the substance is emitted out of the at least one substance delivery member.

In some embodiments, the method may further involve, after the advancing step, changing a shape-changing portion of the treatment device from a delivery configuration in which the shape-changing portion is predominantly straight or otherwise shaped to be not in contact with an inner wall of the blood vessel to a treatment configuration in which at least part of the shape-changing portion contacts the inner wall of the blood vessel at the target location. In some embodiments, changing the shape-changing portion may involve expanding an expandable member on the treatment device to contact the inner wall of the blood vessel. In some embodiments, changing the shape-changing portion may involve forming the shape-changing portion into approximately a circle, where a radius of the circle is approximately perpendicular to a longitudinal axis of a proximal portion of the treatment device, and where a circumference of the circle is approximately as large as a circumference of the inner wall of the blood vessel at the target location. Some embodiments may further involve allowing blood to flow through or past the treatment device while it is in the treatment configuration, to allow perfusion of lung tissue distal to the target location.

In some embodiments, using the treatment device to decrease activity of at least one sympathetic nerve, nerve fiber or neuron comprises altering the nerve, nerve fiber or neuron by a mechanism such as, but not limited to, irreversible electroporation, necrosis, apoptosis, gene expression alteration, cytokine up regulation or downregulation alteration, ablation, electrofusion and/or combinations thereof. In some embodiments, ameliorating pulmonary hypertension may involve decreasing pulmonary vascular resistance in at least one artery of the pulmonary vasculature.

In another aspect, a method of reducing pulmonary vascular resistance may involve decreasing activity of at least one sympathetic neuron innervating at least one blood vessel of the pulmonary vasculature. In some embodiments, reducing pulmonary vascular resistance may involve ameliorating pulmonary hypertension. In some embodiments, the blood vessel may include, but is not limited to, a pulmonary trunk, a right pulmonary artery, a left pulmonary artery, an artery branching from the right pulmonary artery, an artery branching from the left pulmonary artery, and/or any artery branching from the branching arteries.

In some embodiments, decreasing activity of at least one sympathetic neuron may involve advancing a denervation catheter to a target location in the at least one blood vessel and using the denervation catheter to decrease activity of at least one neuron innervating or located near the at least one blood vessel. Some embodiments may further involve contacting an inner wall of the blood vessel with the denervation catheter before using the catheter to decrease activity of the at least one neuron. IN some embodiments, contacting the inner wall may involve expanding an expandable member on a distal portion of the catheter. In alternative embodiments, contacting the inner wall may involve changing a shape of a distal portion of the catheter from predominantly straight to curved, such that an outer diameter of the distal portion in the curved shape contacts the inner wall.

In some embodiments, decreasing activity of the at least one neuron may involve treating the neuron with energy applied from outside a body of a patient. In some embodiments, decreasing activity of the at least one neuron may involve accessing the at least one neuron from outside the at least one blood vessel with a denervation device and using the denervation device to decrease activity of the at least one neuron. For example, accessing the neuron from outside the blood vessel may involve advancing the denervation device through an esophagus. In another embodiment, accessing the neuron from outside the artery may involve advancing the denervation device through a thoracic cavity.

In another aspect, a method of decreasing sympathetic nerve activity in the pulmonary vasculature of a patient to ameliorate pulmonary hypertension may involve: advancing a denervation catheter to a target location in an artery within the pulmonary vasculature of the patient; changing a shape of a portion of the catheter to circumferentially contact an inner wall of the artery with the catheter; and delivering a treatment to at least one sympathetic nerve, nerve fiber or neuron innervating the artery at or near the target location to ameliorate pulmonary hypertension.

In another aspect, a device for decreasing activity of at least one sympathetic nerve, nerve fiber or neuron to ameliorate pulmonary hypertension may include: a flexible, elongate body; a shape-changing member coupled with the elongate body that changes from a first, low-profile configuration for facilitating advancement of the elongate body through a blood vessel to a second, expanded configuration for contacting a wall of an artery, where at least one of the shape-changing member or the elongate body in the second configuration has a diameter at least as large as an average diameter of an inner wall of a right pulmonary artery or a left pulmonary artery; and at least one nerve treatment member coupled with the elongate body for providing a treatment that decreases activity of the at least one sympathetic nerve, nerve fiber or neuron.

In some embodiments, the elongate body comprises at least one member selected from the group consisting of a wire, a hypotube, a coil and a catheter. In some embodiments, the elongate body may have a proximal portion and a distal portion, and the shape-changing member and the at least one treatment member may be coupled with the distal portion. In alternative embodiments, the shape-changing member and the at least one treatment member may be coupled with the proximal portion.

In some embodiments, the treatment member may include an energy delivery member for delivering energy to the nerves, and the energy delivered may be any of the energy forms described above. In some embodiments, the treatment member may include multiple energy delivery members disposed at spaced apart locations along a length of the distal portion of the elongate body. Alternatively, the treatment member may include a substance delivery member for delivering a substance to the nerves. The substance may be any of a number of substances, such as but not limited to the ones described above.

In some embodiments, the shape-changing member may include a deformable member coupled with the distal portion of the catheter for changing the shape of the distal portion from predominantly straight to curved, where a diameter of the curved shape approximates the average diameter of the inner wall of the pulmonary trunk, the right pulmonary artery or the left pulmonary artery. In other embodiments, the shape-changing member may include an expandable member selected from the group consisting of an inflatable balloon, an expandable cage, a malecot, a stent, an expandable ring and an umbrella.

Optionally, the device may further include at least one protective member coupled with a distal portion of the elongate body at or near the treatment member for protecting nearby tissues from unwanted damage. Also optionally, the device may further include a distal protection device coupled with the elongate body and configured to trap material passing distally beyond a distal end of the of the elongate body.

In another aspect, a system for decreasing activity of sympathetic nerves, nerve fibers or neurons to ameliorate pulmonary hypertension, may include a denervation device and a control unit. The denervation device may include: a flexible, elongate body; a shape-changing member coupled with the elongate body that changes from a first, low-profile configuration for facilitating advancement of the elongate body through a blood vessel to a second, expanded configuration for contacting a wall of an artery, where at least one of the shape-changing member or the elongate body in the second configuration has a diameter at least as large as an average diameter of an inner wall of a right pulmonary artery or a left pulmonary artery; and at least one nerve treatment member coupled with the elongate body for providing a treatment that decreases activity of the at least one sympathetic nerve, nerve fiber or neuron. The control unit may be configured for controlling a treatment delivered by the nerve treatment member to decrease activity of the nerves, nerve fibers or neurons in a desired amount while minimizing effects on nearby structures.

In some embodiments, the system may further include a non-transitory computer readable medium within the control unit for directing the control unit to perform a method, which may involve providing a first amount of treatment via the treatment member, and adjusting the treatment member to provide a different amount of treatment. In some embodiments, the treatment member may include an energy delivery member, and the computer readable medium may direct the control unit to provide a first amount of energy and adjust the treatment member to provide a second amount of energy during a treatment. Optionally, the computer readable medium may further configured to direct the control unit to sense the first amount of energy delivered from an energy source to the treatment member and change the amount of delivered energy, based on the sensed amount.

In some embodiments, the system may further include an actuator coupled with a proximal portion of the elongate body and extending to the shape-changing member for changing the shape of the shape-changing member. As discussed above, in various alternative embodiments, the nerve treatment member(s) may include an energy transmission member and/or a substance delivery member.

These and other aspects and embodiments are described in greater detail below, in reference to the attached drawings.

BRIEF DESCRIPTION OF THE DRAWINGS

FIG. 17 is a schematic detail view showing the location of sympathetic nerves relative to a pulmonary artery;

FIGS. 18A and 18B are schematic side- and end-views, respectively, illustrating a direction of electrical current flow for selectively affecting sympathetic nerves innervating the pulmonary vasculature, according to one embodiment;

FIG. 19 is a schematic side-view, partially in section, of an intravascular catheter having a plurality of electrodes, according to one embodiment;

FIG. 22 is a schematic side-view, partially in section, of an intravascular device having an expanding first electrode delivered through the lumen of a catheter and a complementary second electrode carried by the catheter, according to one embodiment;

FIGS. 23A and 23B are a schematic side-view, partially in section, and a detail view, respectively, of an intravascular device having an expandable basket and a plurality of electrodes at the basket, according to one embodiment;

DETAILED DESCRIPTION

Figure 1A:
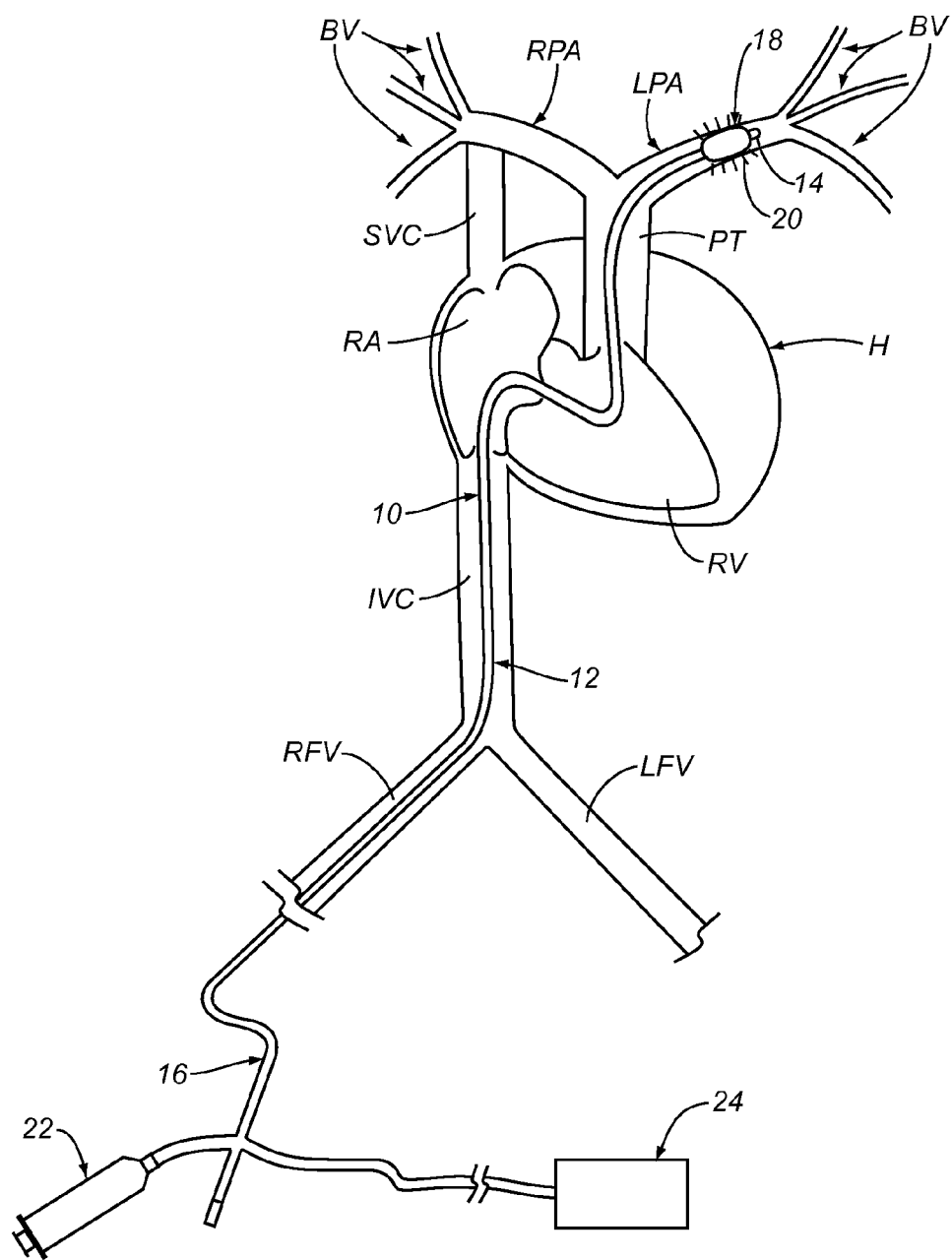
FIG. 1A illustrates a human heart with the pulmonary trunk and right and left pulmonary arteries branching from the pulmonary trunk, along with a catheter device for treating pulmonary hypertension located within the left pulmonary artery, according to one embodiment.

The interplay of the vasoconstrictive/vasodilator axis of the pulmonary circulation is one of the key determinants of pulmonary hypertension disease progression and severity. The sympathetic nervous system mediates pulmonary vasoconstriction. This is specifically accomplished by the thoracic sympathetic chain and branches thereof. The sympathetic nervous system is critical in the mediation of the hypoxia mediated vasoconstrictive response of the pulmonary arterial vasculature. Modulating or reducing the sympathetic nervous system activity within the pulmonary vasculature is a unique approach for the treatment of pulmonary hypertension. Reducing or modulating or negating sympathetic tone to the pulmonary arteries reduces sympathetic mediated vasoconstriction, thereby allowing for increased pulmonary vascular diameter and pulmonary vascular dilatation. The end effect of reducing sympathetic tone is a reduction in pulmonary pressure and pulmonary hypertension, the goal of therapy.

Although this Detailed Description focuses on treatment of sympathetic nerves, nerve fibers and/or neurons, in any given embodiment, a method, device or system described herein may also or alternatively treat parasympathetic nerves, nerve fibers and/or neurons. Therefore, descriptions herein of treating sympathetic nervous tissue should not be interpreted as limiting the scope of the invention.

Pulmonary Neurovascular Anatomy

The sympathetic innervation of the lung and the heart arises from the thoracolumbar spinal column, ultimately reaching the heart and lung and innervating its vasculature. The sympathetic nervous system is part of the autonomic nervous system, comprising nerve fibers that leave the spinal cord in the thoracic and lumbar regions and supply viscera and blood vessels by way of a chain of sympathetic ganglia running on each side of the spinal column which communicate with the central nervous system via a branch to a corresponding spinal nerve. The sympathetic nerves, arising from primarily the thoracic spine, i.e. levels T1-T10 with some potential contribution from the cervical spine, innervate the heart and the lung after branching out from the thoracic sympathetic chain. The sympathetic nerves converge upon the thoracic sympathetic chain and ganglion, after which arise the post ganglionic sympathetic nerves which then innervate the heart and the lung. These nerves often converge upon various plexi, or plexuses which are areas of convergence often of both sympathetic an parasympathetic nerve fibers. These plexuses then further give rise to nerve branches or continuations, which then branch and ramify onto structures within the heart and lung or in association with the outer walls of the pulmonary arteries or arterioles for instance. Some of the key plexuses and their anatomic relationship to the heart, lung, and pulmonary vasculature are described below.

The great plexuses of the sympathetic are aggregations of nerves and ganglia, situated in the thoracic, abdominal, and pelvic cavities, and named the cardiac, celiac, and hypogastric plexuses. They consist not only of sympathetic fibers derived from the ganglia, but of fibers from the medulla spinalis, which are conveyed through the white rami communicantes. From the plexuses branches are given to the thoracic, abdominal, and pelvic viscera.

The cardiac plexus is situated at the base of the heart, and is divided into a superficial part, which lies in the concavity of the aortic arch, and a deep part, between the aortic arch and the trachea. The two parts are, however, closely connected.

The superficial part of the cardiac plexus lies beneath the arch of the aorta, in front of the right pulmonary artery. It is formed by the superior cardiac branch of the left sympathetic and the lower superior cervical cardiac branch of the left vagus. A small ganglion, the cardiac ganglion of Wrisberg, is occasionally found connected with these nerves at their point of junction. This ganglion, when present, is situated immediately beneath the arch of the aorta, on the right side of the ligamentum arteriosum. The superficial part of the cardiac plexus gives branches (a) to the deep part of the plexus; (b) to the anterior coronary plexus; and (c) to the left anterior pulmonary plexus.

The deep part of the cardiac plexus is situated in front of the bifurcation of the trachea, above the point of division of the pulmonary artery, and behind the aortic arch. It is formed by the cardiac nerves derived from the cervical ganglia of the sympathetic, and the cardiac branches of the vagus and recurrent nerves. The only cardiac nerves which do not enter into the formation of the deep part of the cardiac plexus are the superior cardiac nerve of the left sympathetic, and the lower of the two superior cervical cardiac branches from the left vagus, which pass to the superficial part of the plexus.

The branches from the right half of the deep part of the cardiac plexus pass, some in front of, and others behind, the right pulmonary artery; the former, the more numerous, transmit a few filaments to the anterior pulmonary plexus, and are then continued onward to form part of the anterior coronary plexus; those behind the pulmonary artery distribute a few filaments to the right atrium, and are then continued onward to form part of the posterior coronary plexus.

The left half of the deep part of the plexus is connected with the superficial part of the cardiac plexus, and gives filaments to the left atrium, and to the anterior pulmonary plexus, and is then continued to form the greater part of the posterior coronary plexus.

The Posterior Coronary Plexus (plexus coronarius posterior; left coronary plexus) is larger than the anterior, and accompanies the left coronary artery; it is chiefly formed by filaments prolonged from the left half of the deep part of the cardiac plexus, and by a few from the right half. It gives branches to the left atrium and ventricle.

The Anterior Coronary Plexus (plexus coronarius anterior; right coronary plexus) is formed partly from the superficial and partly from the deep parts of the cardiac plexus. It accompanies the right coronary artery, and gives branches to the right atrium and ventricle.

The pulmonary plexuses are the sites of convergence of autonomic fibres which supply the lung. They are in continuity with the cardiac plexuses, which lie superiorly, and the oesophageal plexuses, which lie posterosuperiorly.

They are sited anterior and posterior relative to each lung root. They are in close proximity to the pulmonary arteries and, as they branch laterally they ramify their nerve fibres in association with the outer walls of diverging pulmonary arteries and arterioles.

The passage of fibres from the cardiac plexus is inferiorly, anterior to the trachea and posterior to the aortic arch. The pulmonary plexus also receives autonomic fibres directly from two other sources.

parasympathetic:
right vagus nerve: descends posteroinferiorly on the trachea; divides posterior to the trachea to give pulmonary and oesophageal plexuses; pulmonary plexus passes anteriorly to root of the lung
left vagus nerve: descends anteriorly to arch of aorta, gives off recurrent laryngeal branch and then fibres diverge anteriorly to supply the left pulmonary arterial plexus
sympathetic: rami of the superior four thoracic ganglia pass anteriorly around the posterior thoracic cage to merge on the lateral walls of the oesophagus. They supply nerve fibres to the pulmonary plexus from the region dorsal to the tracheal bifurcation.

It has also been found that the recurrent cardiac nerve and sometimes the craniovagal cardiac nerves carry the main innervation of the pulmonary bifurcation and adjacent parts of the main pulmonary artery and its right and left branches. The recurrent cardiac nerve is a moderately large nerve, arising from the right recurrent laryngeal nerve as it loops around the right subclavian artery. It usually receives a contribution of varying size from the vagal, parasympathetic trunk and another from the stellate ganglion. The nerve passes dorsally to the anterior vena cava, laterally to the brachiocephalic artery and arch of the aorta, to the pulmonary bifurcation to where it divides into anterolateral and posterolateral branches. The anterolateral branch tends to be smaller. The branches then tend to fan out over the anterior and posterior aspects of the main pulmonary artery and communicate with plexi around the right and left pulmonary arteries and the pretracheal plexus. Some fibres continue to the heart and the coronary plexi. During its course, it communicates freely with the cranio-vagal cardiac nerves.

The right vagal cardiac nerves arise from the right vagus trunk caudal to the origin of the right recurrent laryngeal nerve. They fall into two groups, the cranial and caudal vagal cardiac nerves. These vary in size, number, and course. Including some of the smaller divisions, they supply branches or twigs, to the right pulmonary artery plexus, the antero and posterolateral branches of the right recurrent cardiac nerve at the pulmonary bifurcation, and to the plexus formed by the ventral branch of the vagus, anterior to the pulmonary root, and then terminate in the atrial wall. Small twigs or branches, variable in size and position and sometimes absent, are supplied to the pre-tracheal plexus and the plexus around the right and left pulmonary artery by the right stellate cardiac nerves, the venteromedial cervical cardiac nerve, the left recurrent laryngeal nerve, and the ventral branch of the left vagal trunk. Other twigs or branches are supplied from a diffuse plexiform network of fibres form the ventrolateral cardiac nerve and the left stellate cardiac nerve.

One of the most important of these nerves is the recurrent cardiac nerve, especially the right recurrent cardiac nerve, as it can contain pre-ganglionic, afferent and sympathetic post-ganglionic fibres among others. The recurrent cardiac nerve is a branch of the right recurrent laryngeal nerve, the nerve of visceral arch VI (ref 7). It is therefore of considerable interest that the main nerve supply to the pulmonary bifurcation sensory area, part of the visceral arch VI, is derived from the recurrent laryngeal nerve, the nerve of visceral arch VI. As the most cephalic part of the pulmonary artery is formed from the posterior and right lateral parts of the bulbus cordis, this vessel is predominantly supplied from the right visceral nerve VI.

More specifically, the pulmonary artery bifurcation and adjacent portions of the right and left pulmonary arteries receive a very rich innervation. On the right side, the most constant nerve trunk to the bifurcation is the right recurrent cardiac nerve. The fibers arise from the vagus or the recurrent laryngeal nerve as it loops around the subclavian artery immediately cuadad to its origin from the brachiocephalic trunk. The nerve proceeds medially and caudally passing dorsal to the superior vena cava and lateral to the origin of the brachiocephalic trunk. The fibers ramify at the bifurcation by dividing into antero-lateral and postero-lateral branches which communicate with the fibers from the pulmonary plexuses. During its course it communicates with one or more right vagal cardiac nerves, usually of very small size, and branches from the stellate ganglia or ansa subclavia. These latter branches are thought to contribute the efferent component. Minor variation in the mode of origin from the recurrent laryngeal nerve (RLN) were noted. In some cases, the nerve can arise as a separate trunk from the loop of the RLN and can be joined by a cardiosympathetic branch from the adjacent stellate ganglion. The recurrent cardiac nerve can rarely arise from the angle of origin of the RLN as well. In some cases, the major portion of the nerve can arise from the vagus as the vagal cardiac nerve, also receiving a small filament from the RLN.

The contribution to the innervation of the pulmonary artery from the left side is similar to that of the right, but also receives in some cases invariably a small, direct contribution from the vagus in the form of the ventro-medial-cervical cardiac nerve. This nerve arises from the vagus by a variable number of roots, usually two, and proceeds caudally passing over the aortic arch to ramify over the ligamentum arteriosum, pulmonary bifurcation and left pulmonary artery. The superior cranio vagal root usually receives a direct branch from the left stellate ganglion. The bifurcation and left pulmonary artery receive a small inconstant branch from the RLN as it passes under the aortic arch. In some cases, the descending branches arise from the ascending portion of the RLN to terminate around the bifurcation.

It has been further found that the musculature of the pulmonary artery receives a right sided innervation of predominantly vasoconstrictor adrenergic sympathetic fibers, but little to no motor innervation from the parasympathetics or vagus nerve. The fibers synapse mainly in the stellate, but also in the upper thoracic and sympathetic ganglia. It has also been noted that a large concentration of nerve endings are found at the bifurcation of the pulmonary artery, as well as in parts of the adjacent pulmonary artery and its right and left main branches.

Beyond the main pulmonary artery, right main and left main pulmonary arteries, the innervation of the further branches of the lung follows the arterial anatomy, with the nerves coursing along the arteries, typically following a peri-adventitial location or coursing along the adventitia. A rich innervation has been described in pulmonary arteries further distal and to pulmonary arterioles as small as 30 microns in diameter or smaller. This innervation consist both of parasympathetic and sympathetic innervation, with the lungs considered to have a rich sympathetic nerve supply.

Thoracic sympathectomy is a surgical procedure that currently exists and is utilized in the treatment of a different disease process, namely hyperhidrosis syndrome (excessive sweating). Extensive research on this surgical procedure has shown it to be safe and efficacious. Physiological studies of patients undergoing thoracic sympathectomy have shown mild changes in pulmonary function and mild increases in airway resistance, small decreases in heart rate however preserved left ventricular function and ejection fractions, and also preserved exercise tolerance. Data from T2-T3 video assisted thoracoscopic sympathectomy patients have shown that sympathectomy results in severing the ipsilateral hypoxia mediated vasoconstrictive pathway to the pulmonary vasculature by demonstrating a drop in arterial oxygen saturation during contralateral selective lung ventilation both prior and subsequent to sympathectomy. This implies ipsilateral pulmonary vascular dilatation and reduction in pulmonary pressure. Although thoracic sympathectomy has been used for treating hyperhidrosis, it has not been described, prior to the provisional patent application from which this application claims priority, for treating pulmonary hypertension. More generally, decreasing activity of one or more sympathetic nerves or neurons to reduce pulmonary vascular resistance and/or to ameliorate pulmonary hypertension has not been described previously.

Description of Embodiments

The methods described herein involve modulating or reducing the sympathetic tone innervating the pulmonary vasculature by accessing the thoracic sympathetic chain or branches thereof and modulating or reducing sympathetic tone in order to treat pulmonary hypertension. A method to modulate or reduce thoracic sympathetic tone innervating the pulmonary vasculature would likely result in a reduction of pulmonary vascular tone and a reduction in pulmonary arterial pressure and pulmonary hypertension. This reduction of sympathetic tone is also referred to herein as reducing activity of at least one sympathetic nerve or neuron. Again, in some embodiments, sympathetic and parasympathetic nerves may be treated, and in other alternative embodiments, parasympathetic nerves alone may be treated. In some embodiments, nerves may be treated at a neuron-by-neuron level. In some embodiments, whole nerves may be treated. For the purposes of this disclosure, the phrase "nerves or neurons" will not be repeated continuously. Instead, it will be assumed that any embodiment described herein may be used to treat one or more whole nerves, one or more nerve fibers, and/or one or more neurons. This description will thus often refer to "a nerve" or "nerves" generically to encompass any such embodiment.

In some embodiments, neurons or nerves will simply be down-regulated. Alternatively, in other embodiments, reducing thoracic sympathetic tone innervating the pulmonary vasculature may involve partially or completely destroying one or more sympathetic nerves (or neurons) innervating the pulmonary vasculature. This process of partial or complete nerve destruction may be referred to herein as "denervating" or "denervation of" a structure. For example, in some embodiments, the therapy may involve denervating one or more arteries supplying the lungs, such as but not limited to the pulmonary trunk, the left pulmonary artery and/or the right pulmonary artery. In alternative embodiments, one or more veins returning blood to the heart from the lungs may be denervated. This method of modulating or reducing thoracic sympathetic tone innervating the pulmonary vasculature is a unique method for the therapy of pulmonary arterial hypertension.

A number of examples of embodiments are provided herein. No one example should be interpreted as limiting the scope of the invention as it is set forth in the claims. For example, one exemplary embodiment may be described as denervating a pulmonary artery. This same embodiment may be used, in another embodiment, to decrease activity of a neuron of a pulmonary vein. As another example, the phrases "pulmonary hypertension," "treating pulmonary hypertension" and "ameliorating pulmonary hypertension" may be used throughout this disclosure. "Pulmonary hypertension" will generally encompass any and all forms and subsets of hypertension effecting the pulmonary vasculature. Thus, if the phrase "pulmonary artery hypertension" or the acronym "PAH" is used in some examples, this phrase is used for exemplary purposes only, and other embodiments may address other forms or subsets of pulmonary hypertension. Furthermore, in some embodiments, the methods described herein may be used generally for reducing pulmonary vascular resistance, irrespective whether pulmonary hypertension is treated. Thus, the examples provided herein are for exemplary purposes and should not be interpreted as limiting the scope of the invention as it is set for the in the claims.

Referring now to FIG. 1A, in one embodiment, a system 10 for decreasing activity of one or more sympathetic nerves may include an elongate, flexible body 12 having a distal end 14 and a proximal end 16, a shape-changing member 18 at or near distal end 14, a treatment member (not visible) attached to, embedded within or integral with shape-changing member 18, an actuator 22 for changing the shape of shape-changing member 18, and a treatment controller 24 for actuating the treatment member to provide the treatment to decrease activity of the nerve(s). In the embodiment shown, for example, shape-changing member 18 is an inflatable balloon, actuator 22 is a syringe for inflating the balloon with an inflation substance, the treatment member is an energy delivery device for delivering energy 20 to the nerve(s), and controller 24 is an energy source for providing energy to the treatment member.

The access pathway illustrated in FIG. 1A is but one example of many possible access pathways for use with system 10 or alternative embodiments of system 10. In this embodiment, elongate body 12 is advanced through an access point in a peripheral vessel, such as the right femoral vein RFV, into the inferior vena cava IVC, through the right atrium RA of the heart H, into the right ventricle RV, and then through the pulmonary trunk PT to the left pulmonary artery LPA. (Other anatomical structures labeled are the right pulmonary artery RPA, branching vessels BV, superior vena cava SVC and left femoral artery LFA.) Elongate body 12 is generally advanced through the vasculature and heart to a target location in the vasculature. This target location may be any of a number of locations in various embodiments, such as but not limited to the pulmonary trunk PT, left pulmonary artery LPA, right pulmonary artery RPA, any of the branching vessels BV, the ostia of the left or right pulmonary artery, or the like. In alternative embodiments, a different access method may be used and a pulmonary vein or other pulmonary veinous vasculature may be the target location. Many different access routes and potential targets are described in further detail below.

Figure 1B:
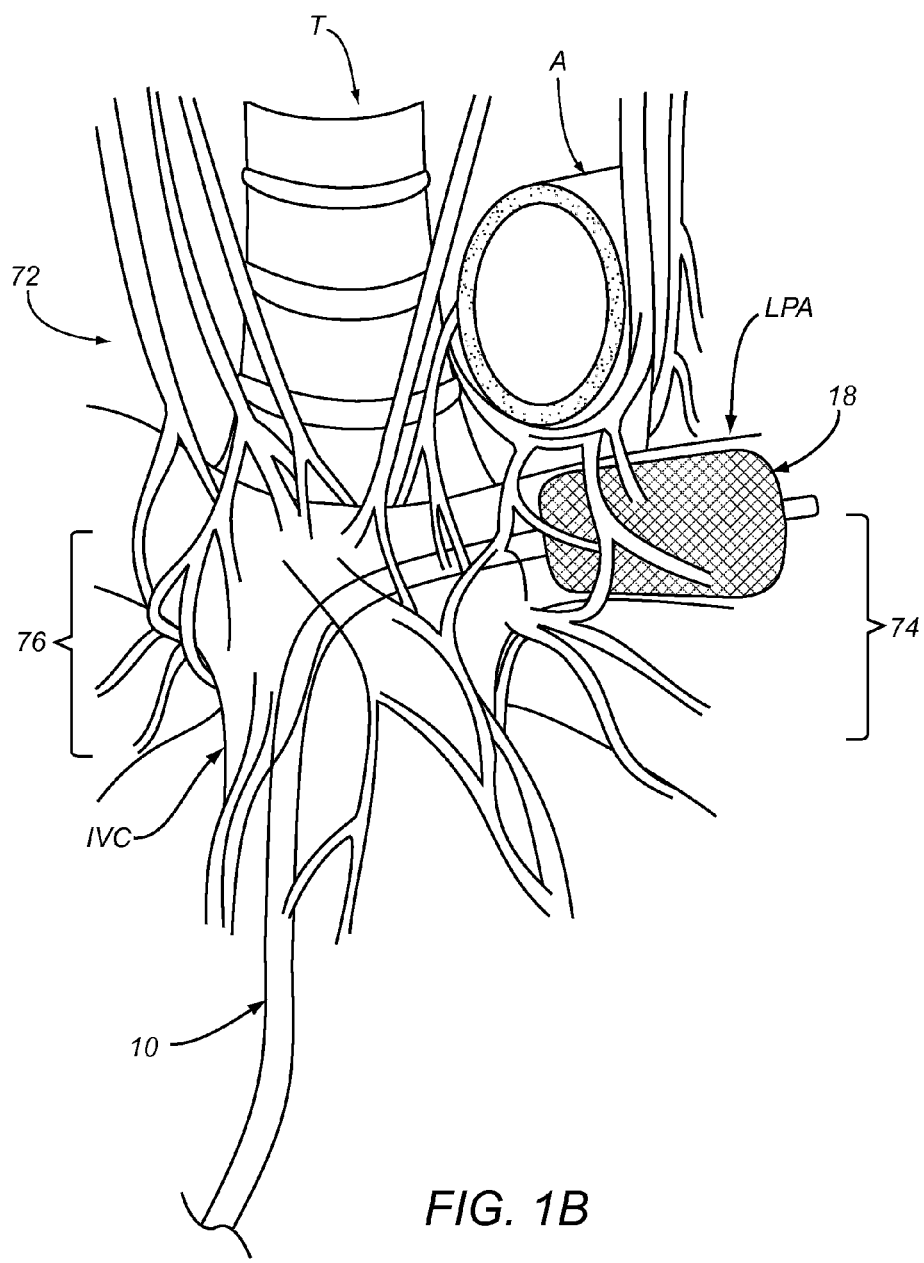
FIG. 1B is a magnified view of some of the anatomy shown in FIG. 1A, from a slightly different view and illustrating various nerves in more detail.

FIG. 1B illustrates some of the anatomy of FIG. 1A in greater detail, along with device 10 and shape-changing member 18. Illustrated in FIG. 1B are an anterior pulmonary plexus 76 and a posterior pulmonary plexus 74, both of which are different nerve plexuses residing near the pulmonary arteries. As illustrated in this figure, the trachea T and aorta A are also located nearby, offering potential other access routes to anterior pulmonary plexus 76 and posterior pulmonary plexus 74. The carina 72 (actually located behind the inferior vena cava IFC as it branches into the left pulmonary artery LPA and right pulmonary artery RPA) is the location where the trachea T branches into left and right bronchi. This, too, may be a target location for a nerve treatment therapy in some embodiments.

Once elongate body 12 is advanced to a target location in the pulmonary vasculature, actuator 22 may be used to change the shape of shape-changing member 18 from a predominantly straight (or "low-profile," "delivery" or "non-contacting") configuration to an expanded, curved, looped or otherwise shape-altered configuration. In the expanded or otherwise altered configuration, shape-changing member 18 either contacts the inner wall of the blood vessel at the target location itself or causes a distal portion of elongate member 12 to contact the inner wall. For example, in the embodiment shown, shape-changing member 18 is an inflatable balloon so contacts the inner wall of the left pulmonary artery itself. In an alternative embodiment, shape-changing member 18 may be a wire or multiple wires positioned within a catheter, such that the wire(s) may be used to alter the shape of the distal portion of the catheter. In one embodiment, for example, one or more shape memory wires, such as Nitinol wires, may be embedded in the distal portion of elongate member 12 and constrained in a relatively straight configuration during advancement of elongate member 12. The wire(s) may then be released from constraint by actuator 22, thus causing the distal portion of elongate body 12 to assume a wall-contacting shape, such as a circle, a spiral or the like. Any of a number of different structures may be used for shape-changing portion 18 in various alternative embodiments, such as but not limited to an inflatable balloon, an expandable cage, a malecot, a stent, an expandable ring and an umbrella.

Changing the shape of shape-changing member 18 to contact the inner wall of the target vessel may have a number of advantages. For example, contact with the vascular wall may help stabilize elongate member 12 within the vessel to help it maintain its position, which may help with accuracy of treatment. Additionally, it may help position one or more treatment members near the nerve or nerves to be treated. Typically, the nerves being treated are located on or within the outer surface of the blood vessel along which they run. Thus, expanding or otherwise changing the shape of shape-changing member 18 to contact the inner wall of the vessel positions the treatment member(s) closer to the outside of the vessel that if the treatment member(s) were instead "floating" within the vessel. Finally, in embodiments where the treatment member of system 10 is an energy delivery device, it will generally be easier and more efficient and accurate to transmit energy directly through the wall of blood vessel with a device that is contacting the inner wall of the blood vessel, rather than trying to transmit through blood or other fluid in addition to the vascular wall. On the other hand, in alternative embodiments, a treatment member and/or shape-changing member 18 may partially or entirely not contact the inner wall of the vessel.

In various alternative embodiments, elongate member 12 may take any of a number of suitable forms. For example, in one embodiment, elongate member 12 may be a flexible catheter. In another embodiment, elongate member 12 may be a flexible wire, such as a Nitinol wire. In either of these two examples, elongate member 12 will generally include at least one lumen, such as an inflation lumen and a lumen through which the treatment member is connected to controller 24. In the wire embodiment, for example, elongate member 12 may be made wholly or partially of a Nitinol hypotube. In some embodiments, elongate member 12 may include both a catheter and wire and/or may be made of a hypotube, a coil or a combination of any of these components.

The diameter of elongate member 12 will be selected to facilitate advancement through any vasculature, valve(s) and other structures necessary to access the target location. Typically, the diameter of elongate member 12 will differ from the proximal end 16 to the distal end 14, with the former generally having a larger diameter to facilitate pushability and the latter having a smaller diameter to facilitate advancement through small structures and to prevent trauma during advancement.

In general, flexible catheters, wires (such as guidewires) and hypotubes are well known by those skilled in the art and thus will not be described in detail herein. Similarly, catheters and wires with expandable balloons, cages and other expandable members are also well known and thus will not be described in detail. What has not been described previously is a method for using such devices for decreasing sympathetic nerve activity to treat pulmonary hypertension.

In general, system 10, device components making up system 10, the access method, and/or the treatment method described above may be altered in any of a large number of ways without departing from the scope of the invention as it is set forth in the claims. For example, many different devices, systems and methods have been described for denervating arteries in other parts of the body for treating one or more conditions other than pulmonary hypertension. One category of such devices, systems and methods, for example, has been described for denervation of pulmonary arteries to treat systemic hypertension. Some examples of such systems have used RF energy, ultrasound, microwave, chemical and other means to denervate pulmonary arteries from within the arteries themselves. Other examples have been described for treating pulmonary nerves from outside the body, such as with high-intensity focused ultrasound (HIFU). On the other hand, applicants are not aware of any previous description of using a device to decrease activity of sympathetic nerves to ameliorate pulmonary hypertension. Therefore, in any given embodiment, any of the devices, systems or methods described for other uses and/or other parts of the body may be adapted for use as part of the methods described herein.

As mentioned above, FIG. 1 illustrates merely one embodiment of system 10, an access route and a target location/structure for treating one or more sympathetic nerves. In alternative embodiments, any of a large number of alternative devices, access routes or methods and/or target locations or structures may be part of the treatment methods described herein. Immediately below is a description of several examples of access methods. Farther below are descriptions of various nerve treatment methods, devices and system components, according to various embodiments.

Examples of Methods of Access

There are multiple potential methods of accessing the sympathetic nervous system as it relates to innervating the pulmonary vasculature. The sympathetic nervous system (SNS) innervating the pulmonary vasculature can be modulated or destroyed by approaching it at several distinct and different anatomic levels. Anatomic levels relevant to the innervation of the pulmonary vasculature include the cervical SNS, the cervicothoracic ganglion, the upper thoracic SNS, and distal branches of the SNS innervating the pulmonary arteries and pulmonary vasculature.

Known surgical approaches or modifications of various surgical approaches could be used to gain access to the SNS at various levels. Open surgical approaches for access to the SNS are well understood, well documented, and well known to thoracic surgeons. Open surgical approaches most often are performed through an antero-lateral or posterolateral thoracotomy, and less frequently through a sternotomy. Additionally, more recently, video assisted thoracoscopic sympathectomy has been described and rapidly adopted as a more minimally invasive means of surgically accessing the sympathetic chain.

Examples of Approaches to the Cervical SNS

One important target is the cervicothoracic paravertebral sympathetic chain encompassing the lower cervical (C5-C8) and upper thoracic (T1-T6) sympathetic ganglia, which are the primary nerves that affect the pulmonary circulation. The upper cervical ganglia can be accessed and approached in several ways.

One such open surgical approach is described below:
1. A ~5 cm incision is made in the lower lateral neck with a knife, and the subcutaneous and superficial muscle layer (platysma) are also incised.
2. The sternocleidomastoid, strap muscles, omohyoid muscles, thyroid and parathyroid glands are retracted away from the trajectory toward the lower cervical vertebral bodies.
3. The contents of the lower cervical carotid sheath, as well as the esophagus, are identified. The carotid sheath is opened to expose the sympathetic nerves wrapping around the carotid artery. These nerves are now exposed for modulation or destruction.
4. The lower cervical vertebral body of interest is identified, and the overlying lower cervical sympathetic ganglion and chain located to the side of the vertebral body and next to the carotid sheath are similarly identified and dissected. The nerve is now exposed for modulation or destruction.

Another method of approaching the cervicothoracic ganglion through a supraclavicular approach is described in its entirety by Odero et al.

Another method involves a minimally-invasive image-guided approach, in which:
1. The imaging technique can be via computed tomography (CT), magnetic resonance (MR), or ultrasonography.
2. Under imaging guidance, a "finder" hollow-bore needle is inserted in the lateral neck.
3. Using stable anatomic landmarks, e.g. the vertebral body, the needle tip is guided to just proximal to the area that the sympathetic chain is likely to be located.
4. The needle is exchanged over a metal wire for a plastic catheter, in a standard Seldinger method.
5. A novel wire, in which the tip is connected to an electrical nerve stimulator, is guided to the area of the likely location of the sympathetic chain.
6. Using nerve stimulation (with a downstream effect of the SNS such as systemic blood pressure elevation) and trial-and-error, the sympathetic chain is identified and ready for subsequent modulation or destruction.

Examples of Approaches to the Upper Thoracic SNS

There are several possible approaches to accessing the upper thoracic sympathetic ganglia and chain.

One open surgical approach, involves a standard upper thoracotomy incision and exposure of the paravertebral sympathetic chain. Another surgical approach involving minimally-invasive thoracoscopy, i.e. video-assisted thoracic surgery (VATS), as is performed for the current therapy for hyperhidrosis syndrome.

Another approach to the upper thoracic SNS involves a mediastinal approach or variation of mediastinoscopy. A mediastinal approach or a variation of a mediastinoscopy procedure could also be modified to gain access to the thoracic sympathetic chain. A standard mediastinoscopic approach could be employed, i.e. transcutaneously near the sternal notch, advancing posterior to the sternum and anterior to the trachea as is conventionally performed. The mediastinoscopic dissection then could be carried out laterally and inferiorly adjacent to the trachea and carried posteriorly to access the thoracic sympathetic chain and its branches.

Another minimally-invasive approach involves a single small (1 cm) incision and the insertion of a thoracostomy tube. The insertion of a thoracostomy tube is a standard, well-known procedure to drain and gain access to the thoracic cavity, and would allow for passage of devices into the thoracic cavity that could be navigated near the upper thoracic sympathetic chain.

Another minimally-invasive transesophageal approach, with the bulk of the device remaining in the esophagus but with effectors (e.g. tines, catheters, energy sources) going through the esophagus, would also allow for close proximity access to the upper thoracic sympathetic chain. The esophagus follows an anatomic course in the posterior mediastinum, in close proximity to the vertebral bodies wherein courses the thoracic sympathetic chain. A transesophageal approach, as is employed with upper endoscopy, with a device remaining in the esophagus, would also allow for access in close proximity to the sympathetic chain at this location.

Yet another novel means is through a transvertebral or Para-vertebral approach. As the thoracic sympathetic chain often lies along the vertebral bodies, an access approach, percutaneously or transcutaneously, through the intercostal space, oriented posteriorly near the spine would also allow for access of the sympathetic chain.

Examples of Approaches to the Distal Sympathetic Nerves at the Anatomic Level of the Pulmonary Arteries The sympathetic nerves directly innervating the pulmonary arteries are wrapped around the length and circumference of the vessels. These very distal nerves can be approached in several ways:

Intravascular approaches: An intravascular approach, involving a catheter or wire or other device, either with initial access through the internal jugular, subclavian, or femoral veins, and following trajectory of venous inflow into the lung, i.e. following the passage of blood through the right atrium, tricuspid valve, right ventricle, pulmonic valve, and into the main pulmonary artery and right and left pulmonary artery thereafter would also give access to the pulmonary vasculature and remain in close proximity to the sympathetic chain. Such a method would provide access in close proximity to the end branches of the sympathetic chain innervating the pulmonary vasculature.

Transbronchial/endobronchial approach: Given that the bronchi also gain sympathetic innervation, an endobronchial approach could also gain proximity to the thoracic sympathetic chain. This could be accomplished through a bronchoscopic approach, coursing into the trachea, distal trachea, and bilaterally past the carinal bifurcation. Such an approach would gain easy access to the thoracic sympathetic chain and proximal branches. Distal branches could be accessed through further bronchoscopic advancement into sub selected lobar branches and segmental anatomical branches of the lung.

Examples of Methods, Devices and Systems for Reducing or Modulating Sympathetic Nervous Activity Using a treatment system, such as system 10 shown in FIG. 1 or other systems in alternative embodiments, sympathetic tone (or "activity") may be reduced using any of a number of different methods. For example, in various alternative embodiments, nerve tissue (or individual neurons in some cases) may be destroyed, deactivated or down-regulated by ligation, clipping, neuromodulation, chemical modulation with blocking agents and/or the like. Several examples of methods for treating nerves are described below.

Once accessed through any of the means described in the previous section, sympathetic nerves can be destroyed using various forms of energy. For example, radiofrequency (RF), microwave (MW), light or laser, heat, high voltage field pulses, ultrasound, and cryoablation, could be employed to destroy sympathetic nerve cells. The following describes various energy application means, particular embodiments, and alternative device designs for accessing the targeted anatomy.

Figure 2:
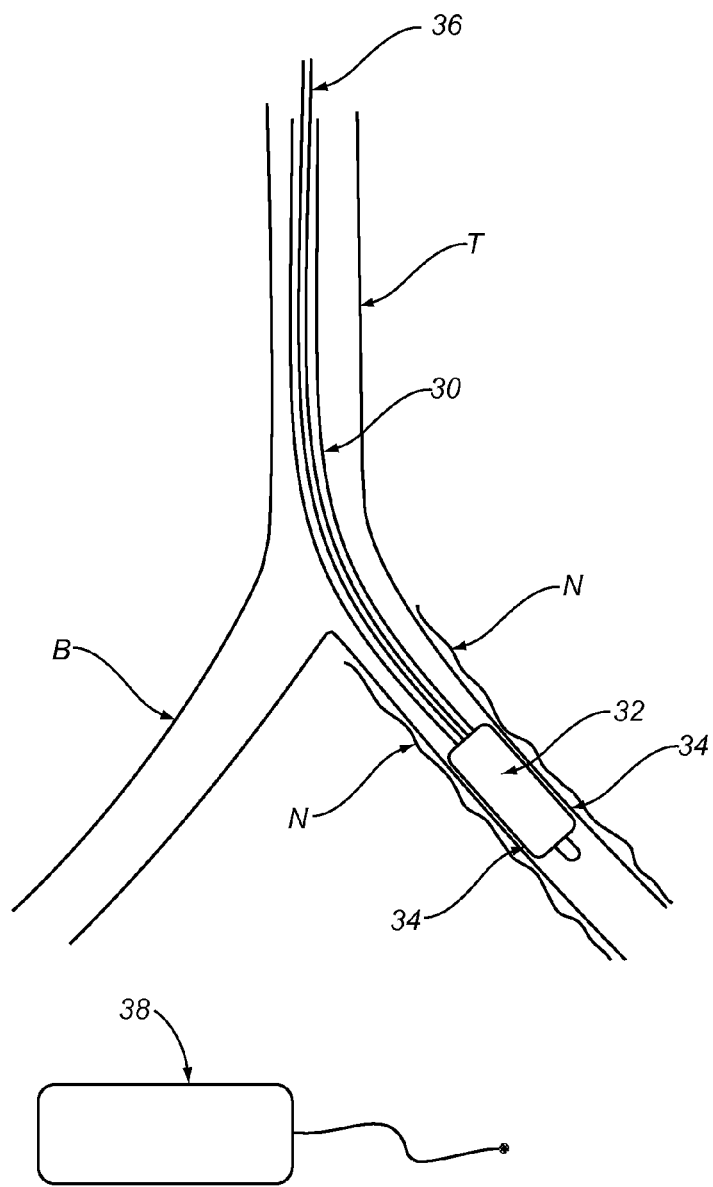
FIG. 2 illustrates a trachea and right and left bronchi with surrounding nerves and other anatomical structures and a nerve tissue treatment device positioned in the left bronchus, according to one embodiment.
Figure 3:
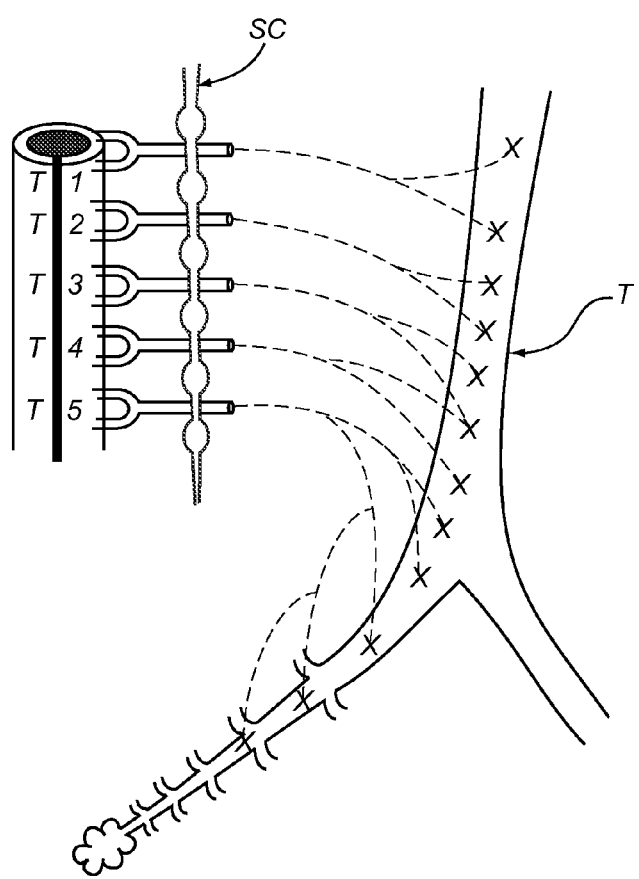
FIG. 3 is a diagrammatic illustration of the trachea and bronchi and a sympathetic nerve chain.

Referring to FIGS. 2 and 3, in one exemplary embodiment, a balloon catheter 30, having an electrode or plurality of electrodes 34 disposed about the periphery of a distal, expandable balloon 32 and wiring 36 or an alternative source of energy may be inserted through a trachea T via a bronchoscope (not shown) into a bronchus B, to target one or more nearby sympathetic nerves N. Referring to FIG. 3, this access route may be used, for example, for targeting regions of the sympathetic chain SC or localized sympathetic innervation via the trachea T. Alternatively, as described above, a similar device could be targeted at nerves disposed about one or more pulmonary arteries or pulmonary veins, or other methods of access described herein may be used for accessing one or more nerves N such as those shown in FIG. 2.

Figure 4:
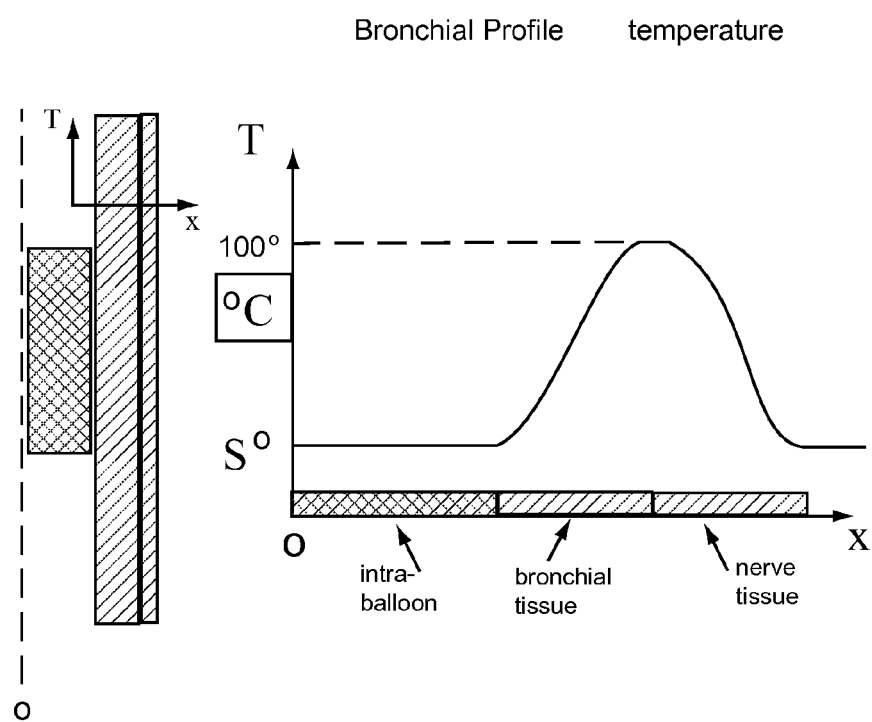
FIG. 4 is a graph illustrating a bronchial temperature profile for treating nerve tissue with a temperature delivery device via the bronchial tree, according to one embodiment.

Referring to FIG. 4, in the embodiment shown, balloon 32 is expanded to engage the bronchial wall and minimize contact impedance between the balloon electrode and the tissue. RF energy, for example, a signal at a frequency of approximately 500 kHz and power of approximately 1-300W, may be delivered for a defined period of time (for example, approximately 5-30 minutes) to heat and destroy the sympathetic innervation surrounding the periphery of the bronchi (or alternatively, pulmonary arteries or veins). In addition, in order to prevent damage to the bronchial (or alternatively arterial or venous walls), it may be desirable to monitor the temperature at the balloon-tissue interface, or alternatively, infuse a substance (e.g. water) at a known, controlled temperature within the lumen of balloon 32 (e.g. 5° C.). Using such an approach, coolant fluid temperature and/or flow rate and/or RF power can be adjusted to maintain a desired temperature profile, where preferably, bronchial tissue is maintained at temperatures <60° C., whereas sympathetic nerve tissue is maintained at temperatures greater than 60° C., as shown in FIG. 4.

In various embodiments, balloon electrodes 34 may be configured in a bipolar configuration about the balloon or, alternatively, in a monopolar configuration, where a separate grounding pad 38 or electrode is placed elsewhere on the patient's body to complete the circuit. In other alternative embodiments, RF energy or any other suitable energy form could be employed to divide the sympathetic nerves, in contrast to the ablative RF mode described above.

Figure 5A:
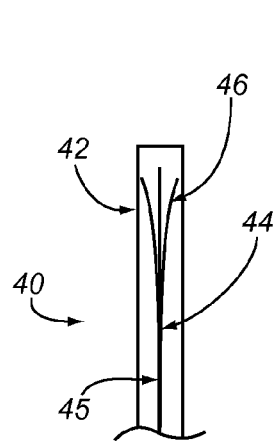
FIGS. 5A-5D are side cross-section, side cross-section, end-on cross section and magnified side views, respectively, of a treatment device including an expanding tissue contact portion, according to one embodiment.
Figure 5B:
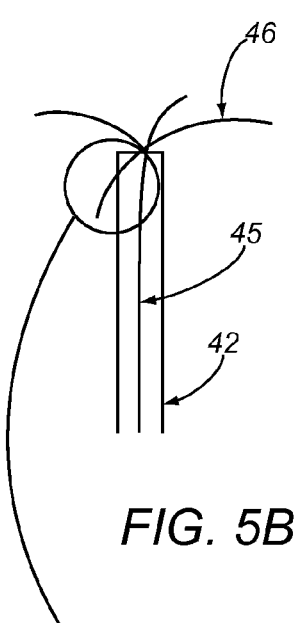
Figure 5C:
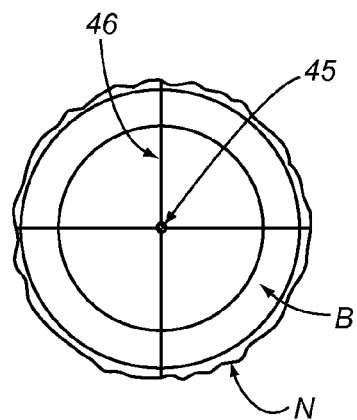
Figure 5D:
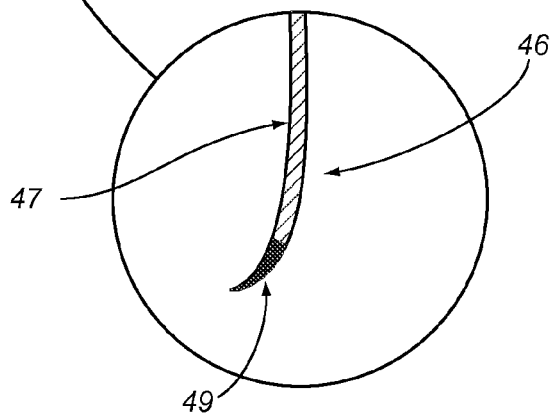
Figure 6A:
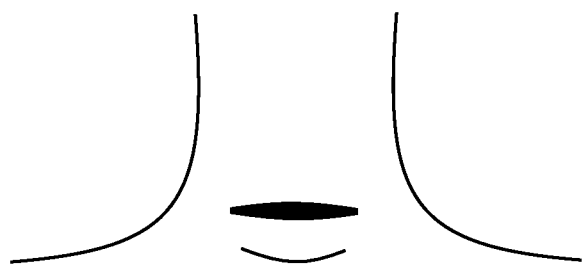
FIGS. 6A-6E are diagrammatic illustrations of a method for accessing a nerve ganglion via the pulmonary tree and removing the ganglion, according to one embodiment.
Figure 6B:
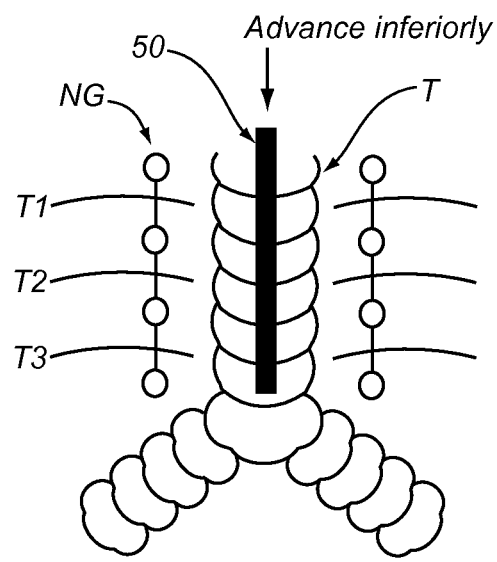
Figure 6C:
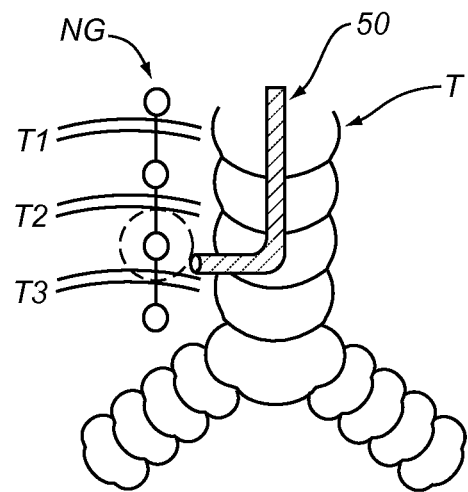
Figure 6D:
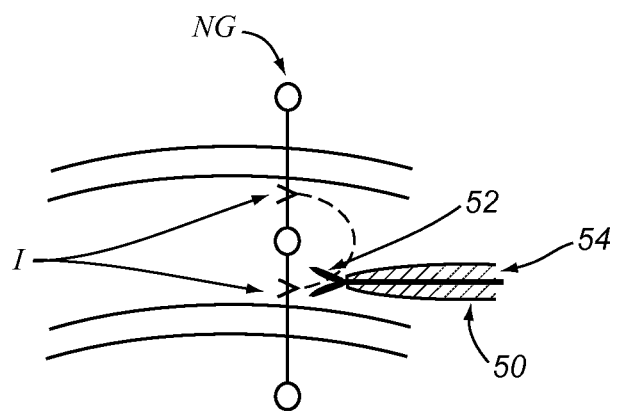
Figure 6E:
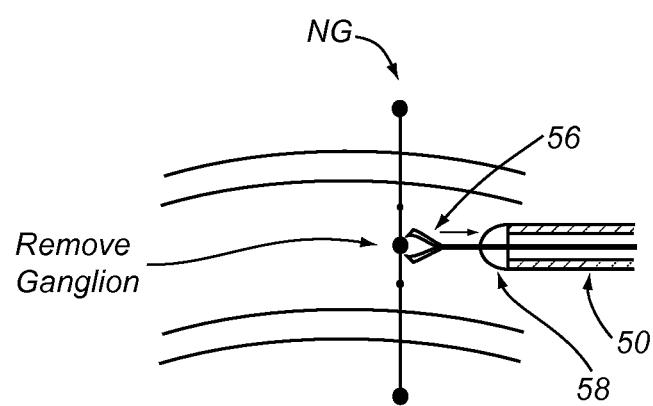

With reference now to FIGS. 5A-5D, in another exemplary embodiment, access may be gained to a bronchus using an endoscope and a catheter treatment catheter 40 may be deployed therein to the target location. Alternatively, such an approach could be realized endovascularly via arterial catheterization under fluoroscopic imaging guidance. Catheter device 40 may include a sheath 42 and an energy delivery member 44 housed within sheath 42. Energy delivery member 44 may include a proximal support wire 45 and multiple, electrically active tines 46 extending from support wire 45. Any suitable number of tines 46 may be included, in various embodiments, and they may emanate from support wire 45 at any suitable angle. FIG. 5A shows energy delivery member 44 in a collapsed/constrained configuration within sheath 42, as may typically be used for delivery of catheter 40 to a treatment location in the body. FIG. 5B shows energy delivery member 44 in an expanded, treatment configuration, with tines 46 extended out of a distal end of sheath 42. As shown in FIG. 5C, tines 46 may be deployed through the wall of the bronchus B and into the nerve tissue N. RF energy may then be applied to ablate and destroy sympathetic nervous tissue N. As illustrated in FIG. 5D, the proximal portions of the tines, in some embodiments, may be substantially (and in some cases adjustably) covered with electrical insulation 47, with only a distal portion 49 exposed, in order to avoid direct ablation of bronchial tissue.

In various alternative embodiments, any other suitable type of energy may be used to treat one or more nerves or neurons, such as but not limited to microwave (MW), laser, high voltage field pulses, heat, cold, electric, electromagnetic, magnetic, direct current, ultrasound and cryoablation. In various embodiments, any of these or other suitable energy types may be employed to destroy sympathetic nerve cells in configurations similar to those described in any of the preceding figures. MW energy in particular (for example a signal in the range of 0.9 to 2.4 GHz at a power of 1-100 W applied through monopole, half-dipole, dipole, or helical coil antenna configurations) may be particularly advantageous when compared to RF, heat, high voltage field pulses, and cryoablation energy delivery in bronchial tissue, due to the low thermal and electrical conductivity of such tissue.

Whereas electromagnetic energy delivery generally induces hyperthermic destruction of nerve cells, direct heat energy (or lack thereof) can be employed to destroy nerve cells through thermal conduction. To induce hyperthermic nerve cell death, a fluid (e.g. water or steam) could be delivered through a balloon catheter device, such as those illustrated in FIGS. 1 and 2, in order to heat and destroy nerve cells at temperatures >60° C. Alternatively, cryoablation can be employed to induce hypothermic cell lysis at temperatures <0° C. For example, using either of the embodiments shown in FIGS. 1 and 2, liquid nitrogen or other fluid at cryogenic temperatures (those <0° C.) may be circulated within the balloon to achieve such an effect.

The energy modalities described herein to destroy nerve tissue could be disposed about other device structures optimized for different access approaches. As illustrated in FIGS. 1, 2 and 5A-5D, catheter designs are employed having distal end effectors configured for energy delivery. Alternatively, for percutaneous access, a needle introducer and energy applicator configuration may be preferable. For laparoscopic access, the energy application means could be disposed about an elongated cannula.

Another method of accomplishing nerve denervation is using a mediastinal approach superior to the relevant anatomy. A mediastinocscope contains a visualization means to navigate the thoracic cavity from a small superior incision at the sterno-clavicular joint. The visualization means allows the operator to perform directed procedures within the thoracic cavity through the use of the working channel in the mediastinoscope. The working channel can accept various tools including cutting means, grasping means, energy-delivery means, etc. By using a cutting and grasping means within the working channel, the nerve ganglion located in the T2/T3 gap can be excised effectively denervating the distal nerve matter.

As an illustrating, but not limiting, example, consider the following sequence of operation, illustrated in FIGS. 6A-6E:
1. Make a small incision I superior to the sternoclavicular joint. [FIG. 6A]
2. Manually spread tissue to provide subdermal access for a mediastinoscope.
3. Insert a mediastinoscope 50 into incision and visually navigate, using visualization means within mediastinoscope 50, inferiorly through the trachea T to the bronchial bifurcation in a manner posterior to sternum and anterior to the trachea. Nerve ganglia NG run along either side of the trachea T [FIG. 6B]
4. Explore laterally with mediastinoscope 50 to expose the sympathetic nerve ganglion located in proximity to the T2/T3 vertebral space lateral to the trachea and adjacent to the spinal column. [FIG. 6C]
5. Incise I the nerve tissue inferior and superior to the nerve ganglion NG to eliminate the nerve conduction using a cutting member 52 passed through a working channel 54 of mediastinoscope 50. [FIG. 6D]
6. Excise the isolated nerve ganglion NG using a grasping member 56 and retract through working channel 54. [FIG. 6E]
7. After locating and excising the first sympathetic nerve ganglion NG, expose the nerve ganglion NG located symmetric about the sagittal plane in the same T2/T3 vertebral space and excise in the same manner.
8. Retract mediastinoscope 50 through the incision.
9. Suture the incision.

While not an exhaustive list, preceding approach may provide at least some of the following advantages:
1. Constant visualization using, for example, a translucent cap 58 on mediastinoscope 50 provides confirmation that the intended nerve ganglion (in the T2/T3 vertebral space) is identified and the correct nerve segment is incised.
2. The visualization is also able to provide confirmatory feedback that the entirety of the nerve segment was incised.
3. The anatomy of the aforementioned regional anatomy is constant between people; therefore, the aforementioned landmarks, such as the tracheal bifurcation, can be used to reliably guide the procedure.

Figure 7:
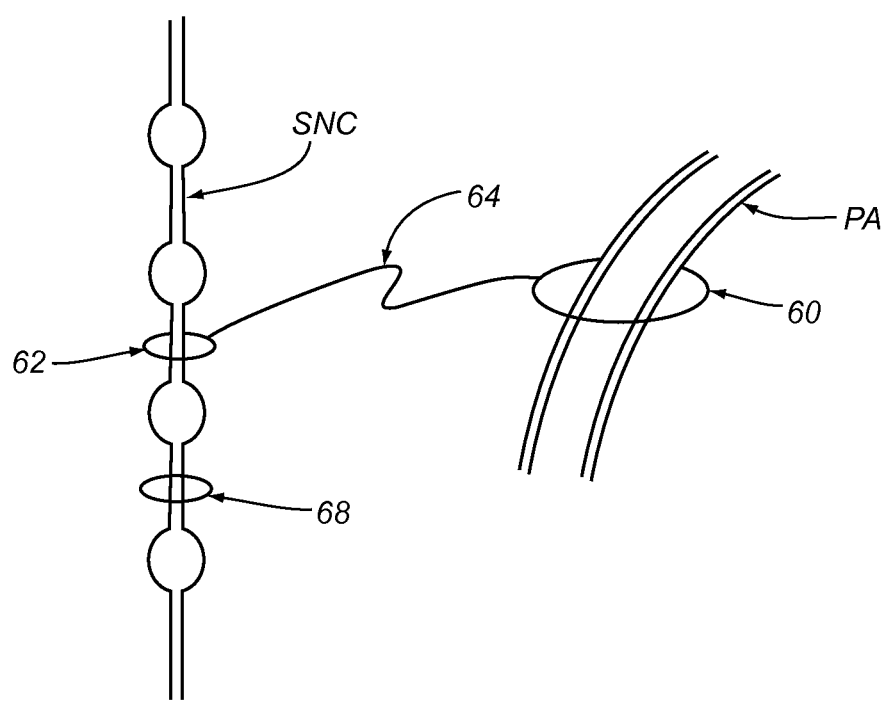
FIG. 7 illustrates a looped nerve constriction device disposed about a pulmonary artery and a sympathetic nerve chain, according to one embodiment.

Referring now to FIG. 7, in contrast to the nerve destruction approaches described above, in some embodiments, it may be desirable to temporarily modulate sympathetic nerve activity rather than permanently destroy nerve fibers. In one embodiment, as illustrated in FIG. 7, a first band 60 may be disposed about a pulmonary artery PA. A complimentary, second band 62 may be disposed about a sympathetic nerve chain SNC. Increases in pulmonary artery pressure may transduced from first band 60 to second band 62 via a connector 64, in such a way to cause restriction of second band 62 about the sympathetic nerve chain SNC, thereby reducing sympathetic activity and maintaining a desirable pulmonary arterial pressure.

Alternatively, in another embodiment, a reversible restriction device 68 may be placed around the sympathetic nerve chain SNC in order to provide adjustable and reversible constriction and modulation of sympathetic activity independent of pulmonary arterial pressure.

Figure 8:
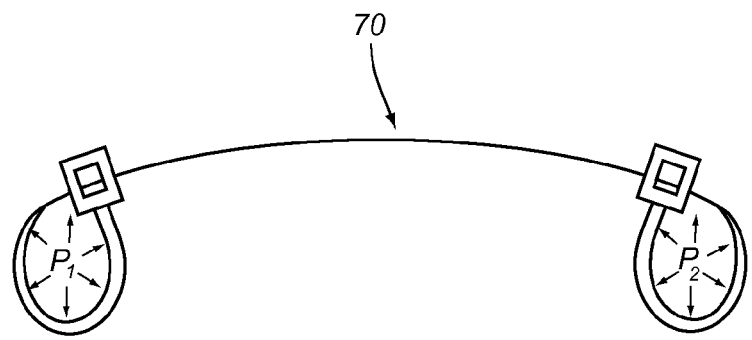
FIG. 8 illustrates an adjustable, two-loop band, according to one embodiment.
Figure 9:
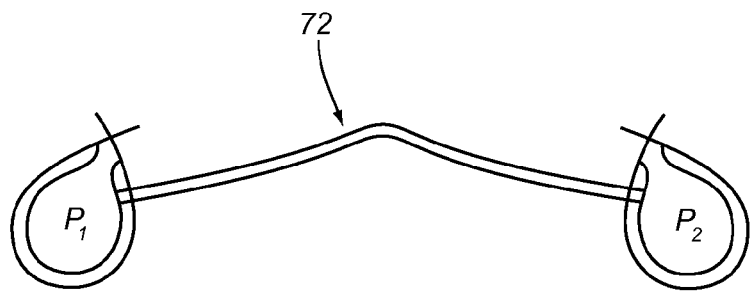
FIG. 9 illustrates an adjustable, two-loop, hydraulic band, according to one embodiment.

With reference now to FIGS. 8 and 9, as an added benefit, in some embodiments, a desired pulmonary arterial pressure set point may be selectively adjustable by the patient or physician. For example, in one embodiment, as in FIG. 8, an adjustable looped band 70 may be provided. In another embodiment, as in FIG. 9, a pneumatic or hydraulic band 72 may be provided. Fluid may be added to or removed from pneumatic/hydraulic band 72 in order to adjust the level of sympathetic constriction and modulation provided for any given level of pulmonary arterial pressure.

Figure 10A:
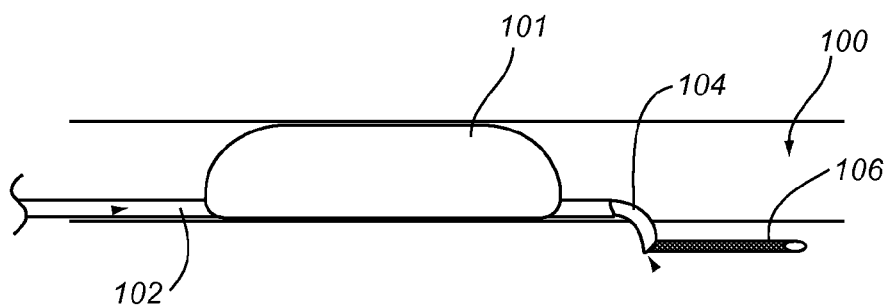
FIGS. 10A and 10B are schematic side-views, partially in section, illustrating methods and apparatus for pulsed electric field neuromodulation via an intra-to-extravascular approach having a bipolar electrode pair with at least one of the electrodes of the pair positioned extravascularly, according to one embodiment.
Figure 10B:
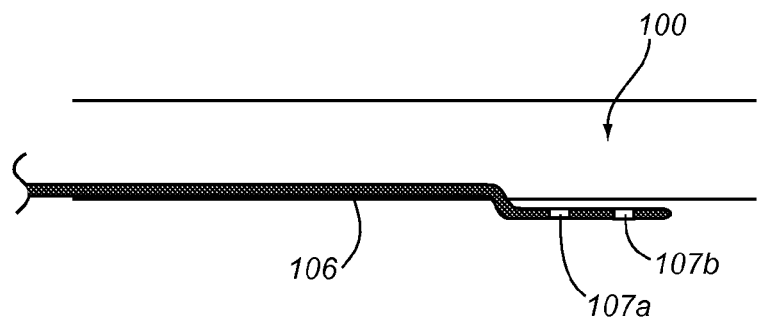

Referring now to FIGS. 10A and 10B, in one embodiment, a treatment system 100 may be configured to provide pulsed electric field ("PEF") neuromodulation via an intra-to-extravascular ("ITEV") treatment system 100. System 100 may include a treatment catheter 102, which optionally may comprise an expandable element 101 (e.g., an inflatable balloon) that stabilizes the catheter 102 within the patient's vessel. The expandable element 101 further facilitates piercing of the vessel wall with the cannula 104 to position the first electrode 106 at an extravascular location. As seen in FIG. 10B, the first electrode 106 may comprise a spaced bipolar electrode pair 107a and 107b to obviate the need for the intravascular second electrode.

The PEF therapy may be delivered extravascularly across the bipolar electrode pair 107a-b.

The extravascular second electrode 106 optionally may be replaced with a virtual electrode. For example, conductive saline may be injected through cannula 104 into the extravascular space. The conductive saline may provide a virtual electrode surrounding all or part of the circumference of the vessel and may be used in a bipolar fashion with intravascular electrode.

Figure 11:
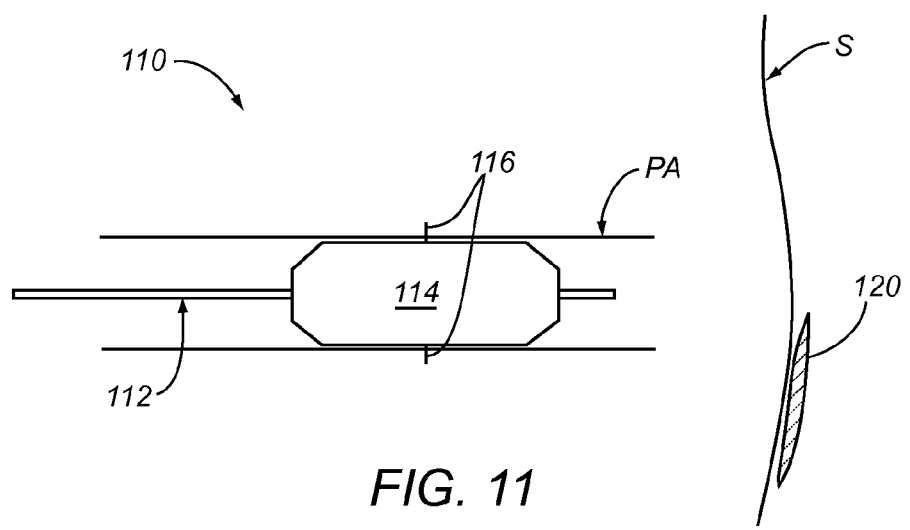
FIG. 11 is a schematic view, partially in section, illustrating methods and apparatus for monopolar pulsed electric field neuromodulation via an intra-to-extravascular approach, according to one embodiment.

FIG. 11 illustrates an alternative monopolar ITEV PEF system 110 comprising a catheter 112 having an expandable element 114 with one or more needle-like ITEV electrodes 116 coupled to the expandable element. When multiple needle electrodes 116 are provided, they may be spaced circumferentially and/or longitudinally about/along the expandable element 114. The system 110 further comprises a ground pad 120 attached to the skin S of the patient along the exterior of the patient (e.g., to the patient's flank, back or thigh) and coupled to the PEF generator 50 as a return electrode. The ground pad 120 optionally may be positioned directly lateral to the ITEV electrode(s) 116 to direct the PEF therapy along the patient's vasculature (e.g., along a pulmonary artery PA).

The expandable element 114 comprises a member or structure configured for intravascular delivery to (and retrieval from) a target location in a low profile configuration and for expansion to an expanded deployed configuration at the target location. The expandable element 114 may comprise, for example, an inflatable balloon, an expandable basket or cage, or other expandable structure. As seen in FIG. 5, expansion of the expansion element 114 causes the ITEV electrode(s) 116 to pierce the wall of pulmonary artery PA and move from an intravascular location to an extravascular location. With the ITEV electrode(s) 116 positioned extravascularly and coupled to the PEF generator 50, the ITEV electrode(s) may be energized as active electrodes in a monopolar PEF therapy with the external ground pad 120 serving as the return electrode.

Figure 12:
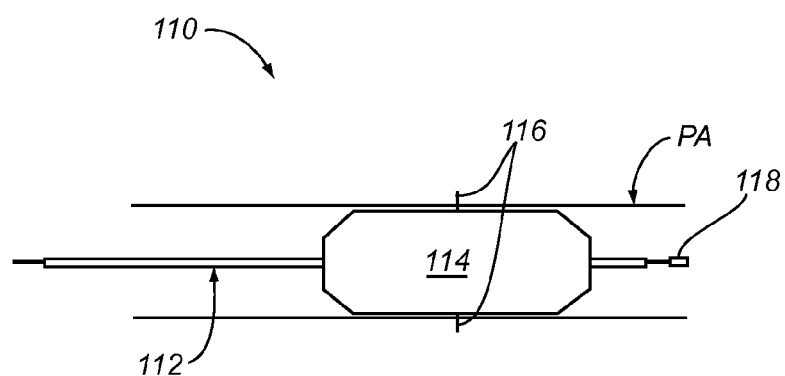
FIG. 12 is a schematic side-view, partially in section, illustrating alternative embodiments of the methods and apparatus of FIG. 11, the methods and apparatus comprising a bipolar electrode pair having a first electrode positioned extravascularly and a second electrode positioned intravascularly.

Referring now to FIG. 12, an alternative embodiment of the ITEV PEF system 110 are described comprising a first electrode positioned extravascularly and a second electrode positioned intravascularly. In FIG. 12, the ITEV PEF system 110 again comprises the catheter 112 having the expandable element 114 with one or more ITEV electrodes 116 coupled to the expandable element and configured for intra-to-extravascular delivery. The system 110 further comprises an intravascular second electrode 118 positioned within the vessel. The second electrode 118 comprises a guidewire electrode positioned within the lumen of the catheter 112. The guidewire electrode 118 is coupled to the PEF generator 50 and is insulated at regions other than a distal region positioned distal of the catheter 112. In use, the ITEV electrode(s) 116 may comprise active electrode(s) and the second electrode 118 may comprise a return electrode, or vice versa. The second electrode 118 optionally may be longitudinally spaced relative to the ITEV electrode(s) 116 to align the PEF therapy with a longitudinal axis of the patient's vasculature. The second electrodes 118 may, for example, be fabricated from wound coils of wire. When utilizing relatively long electrodes, wound coils allow the catheter 112 to maintain desired flexibility.

Figure 13A:
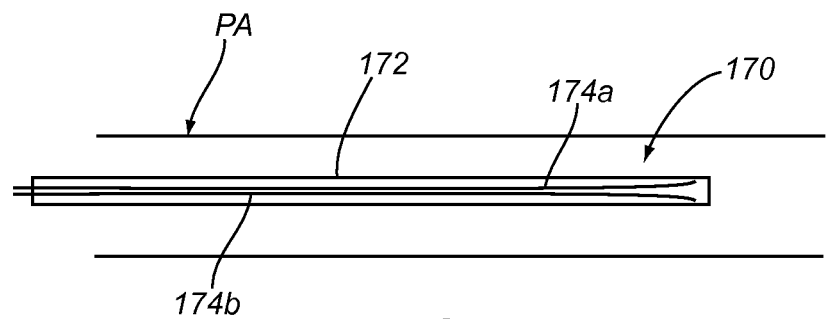
FIGS. 13A-13C are a schematic side-sectional view and schematic side-views, partially in section, illustrating methods and apparatus for pulsed electric field neuromodulation having at least one bipolar electrode pair with both electrodes of each electrode pair positioned extravascularly via an intra-to-extravascular approach, according to one embodiment.
Figure 13B:
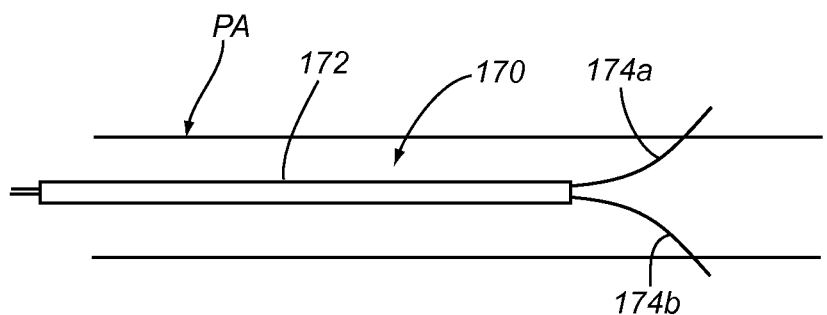
Figure 13C:
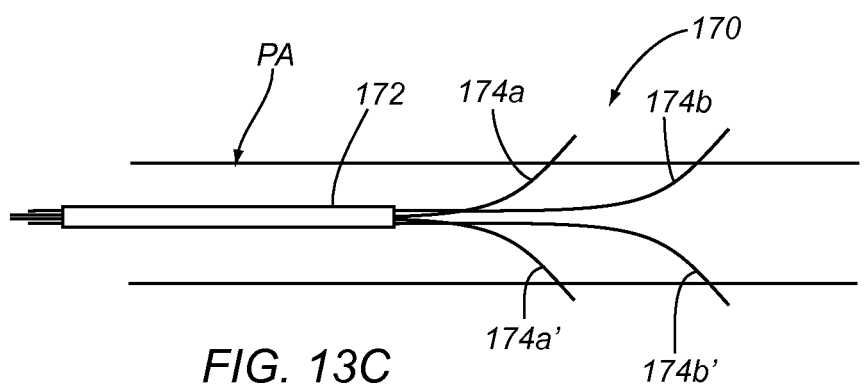

Referring now to FIGS. 13A-C, methods and apparatus for pulsed electric field neuromodulation are described utilizing one or more bipolar electrode pairs with both electrodes of each pair positioned extravascularly via an intra-to-extravascular approach. One example of such an ITEV PEF system 170 comprises a catheter or sheath 172 having shaped ITEV bipolar needle electrodes 174a and 174b that are configured for advancement to an intravascular location within the sheath. The electrodes 174a-b may have shape-memory properties (e.g., may be fabricated from a shape-memory alloy such as Nitinol) and may be insulated at locations other than their distal regions. As seen in FIG. 13B, upon advancement of the electrodes 174a-b to a position distal of the sheath 172 (e.g., via retraction of the sheath), the electrodes 174a-b assume their preformed shape and puncture the wall of the patient's vasculature, illustratively pulmonary artery PA, such that the distal regions of the electrodes 174a-b are positioned extravascularly via an ITEV approach. Electrodes 174a and 174b may be longitudinally spaced relative to one another to better align the PEF therapy with a longitudinal dimension of the patient's vasculature. Furthermore, although the electrodes illustratively are spaced radially about 180 degrees apart, the electrodes alternatively may be spaced with any desired radial separation (or lack thereof).

FIG. 13C illustrates another example of the ITEV PEF system 170 comprising multiple pairs of ITEV electrodes that are longitudinally spaced. The system 170, for example, can comprise a first bipolar electrode pair 174a and 174b, and a second bipolar electrode pair 174a' and 174b'. Additional pairs of bipolar electrodes at different circumferential positions or with different longitudinal spacing may be utilized as desired in other examples.

Once properly positioned, PEF therapy may be delivered across the electrodes 174 to achieve desired neuromodulation. Upon completion of the PEF therapy, the needle electrodes 174 may be retracted relative to the sheath 172, and/or the sheath 172 may be advanced relative to the electrodes 174, such that the electrodes are removed from the wall of the patient's vasculature and coaxed back into a constrained retrieval configuration within the sheath. The ITEV PEF system 170 then may be removed from the body.

Figure 14A:
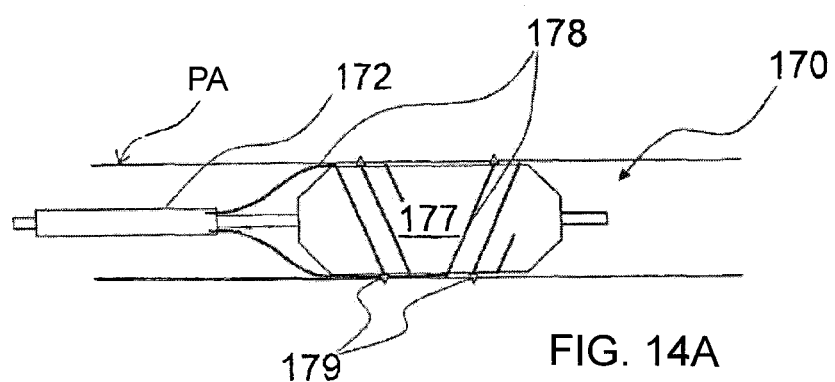
FIGS. 14A and 14B are schematic side-views, partially in section, of embodiments of apparatus comprising multiple pairs of bipolar electrodes.
Figure 14B:
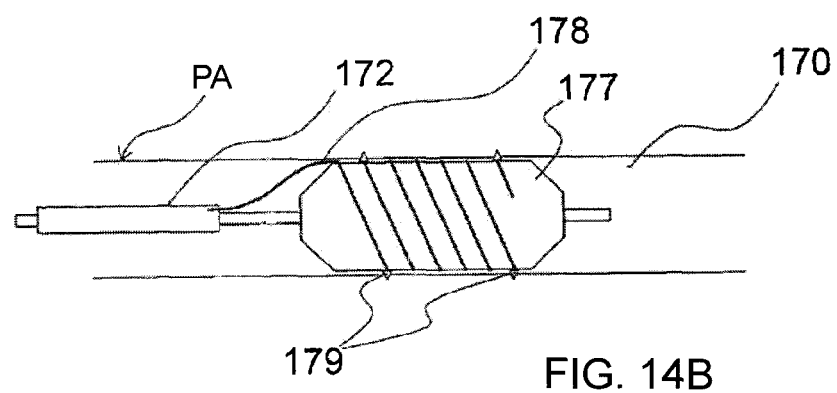

FIGS. 14A and 14B illustrate additional alternative embodiments of the ITEV PEF system 170 comprising multiple pairs of bipolar electrodes. As seen in FIG. 14A, the electrode carriers 178 optionally may spiral around the expandable element 177. The carriers 178 optionally may comprise several electrodes 179 positioned at multiple circumferential positions to facilitate more circumferential PEF therapy. The electrode carriers 178 preferably are electrically isolated from one another. For example, the carriers 178 may be insulated at all regions except for at the electrodes 179.

As seen in FIG. 14B, the system 170 optionally may comprise a single electrode carrier 178 that spirals around the expandable element 177. A plurality of the electrodes along the unitary carrier may be of a common polarity and/or may be electrically isolated from one another and of varying polarity to form bipolar electrode pair(s). The electrodes 179 may be positioned a multiple circumferential positions, as desired. patient to complete the procedure.

With reference to FIGS. 15A-15D, alternative embodiments of the ITEV PEF system 350 are described. In FIGS. 15A-15D, the system 350 includes a catheter 352, an outer sheath 354, an outer shaft 356, at least one expandable member, such as an inflatable balloon 366, and a stent-like element 370 having extensions 359. The balloon(s) 366 alternatively may be used in combination with a hypotube, and/or the stent-like element 370 alternatively may be used in combination with a guide block.

The stent-like element 370 may be completely conductive and may serve as a unitary electrode. Alternatively, the stent-like element 370 may be fabricated from a relatively insulating material with electrode contacts that are etched or deposited onto the element and/or its extensions. A variety of electrode configurations may be provided. Furthermore, the multiple elements 370 (or a combination of hypotubes 358 and elements 370) may be provided. In addition or as an alternative to the deployment mechanisms illustrated in FIGS. 15A-15D, the extensions 359 may be deployed via other deployment mechanisms, such as push/pull mechanisms (e.g., a pull wire) or a pressure/vacuum channel.

Figure 15A:
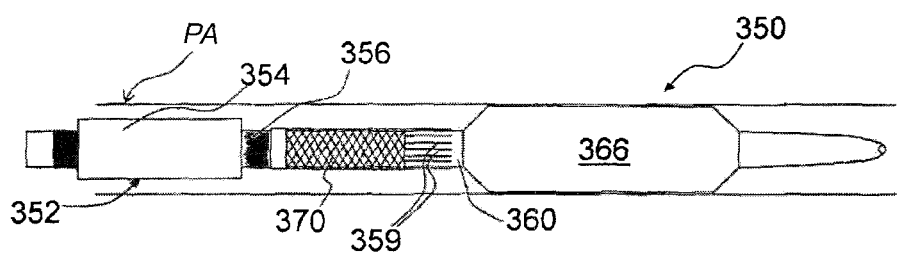
FIGS. 15A-15D are schematic side-views, partially in section, of still further methods and apparatus for pulsed electric field neuromodulation via electrodes positioned extravascularly via an intra-to-extravascular approach, according to various embodiments.
Figure 15B:
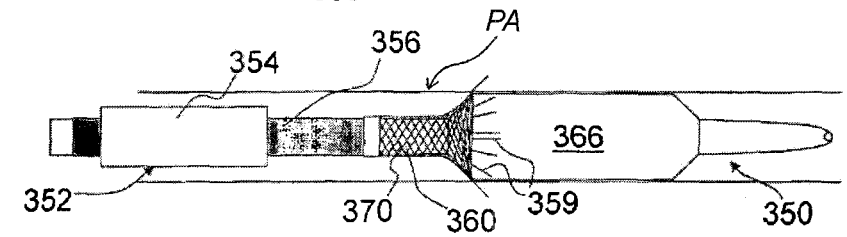

As seen in the embodiment of FIGS. 15A and 15B, the system 350 may be positioned at a treatment site, and the balloon 366 coupled to the inner shaft 360 may be inflated into contact with the vessel wall. As seen in FIG. 15A, the inflated balloon 366 centers the system 350 within the vessel and provides a tapered guide path that provides a smooth transition for deformation of the extensions 359 of the stent-like element 370 during ITEV placement of the extension electrodes. As seen in FIG. 15B, the outer shaft 356 may be advanced relative to the inner shaft 360 such that the extensions 359 begin to deform about the balloon and are directed radially outward. This deformation optionally may be assisted via additional deployment mechanisms, such as pull-wires, to begin deformation of the extensions 359. Continued advancement of the outer shaft 356 relative to the inner shaft causes the extensions 359 to pierce the vessel wall so that the ends of the extension electrodes 359 are positioned extravascularly via an ITEV approach.

Figure 15C:
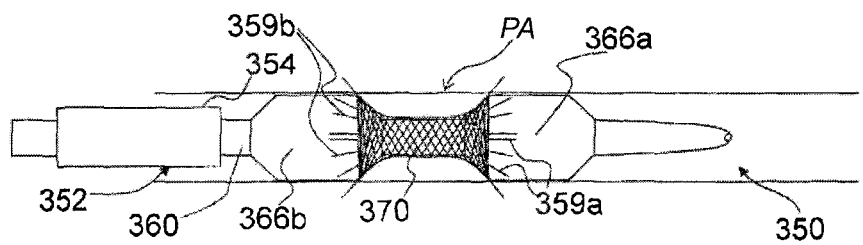

As seen in FIG. 15C, the stent-like element 370 may comprise longitudinally spaced extensions 359a and 359b to provide longitudinally spaced bipolar electrode pairs. In FIG. 15C, the inner shaft 360 comprises distal and proximal expandable elements, illustratively a distal balloon 366a and a proximal balloon 366b. The stent-like element 370 is positioned between the proximal and distal balloon, with the extensions 359a and 359b overlapping the distal and proximal balloons 366a-b, respectively. This overlap obviates a need for the outer shaft 356 shown in FIGS. 18A and 18B. ITEV placement of the extension electrodes 359a-b is achieved by inflating balloons 366.

Figure 15D:
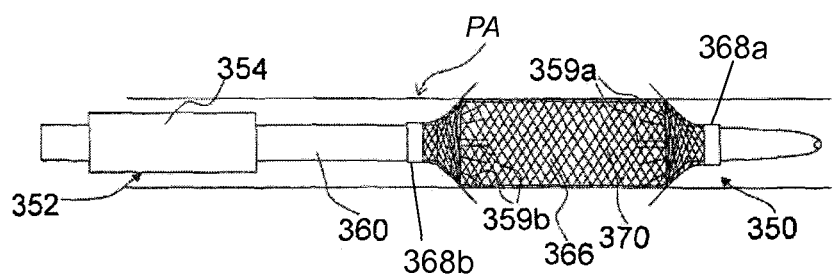

As seen in FIG. 15D, the stent-like element 370 with proximal and/or distal extensions 359 may be positioned over an expandable element, such as inflatable balloon 366. The expandable element 370 may be coupled to the shaft 360 proximally and/or distally (e.g., at a distal collar 368a and at a proximal collar 368b). At least one of the collars 368a or 368b is slidingly coupled to the shaft 360 to facilitate expansion of the expandable element 370 during expansion of the balloon 366. As with the embodiment of FIG. 18C, the positioning of the expandable element 370 relative to the balloon 366 obviates a need for an outer shaft. Rather, ITEV placement of the extension electrodes is achieved by inflating the balloon 366.

Figures 16A, 16B:
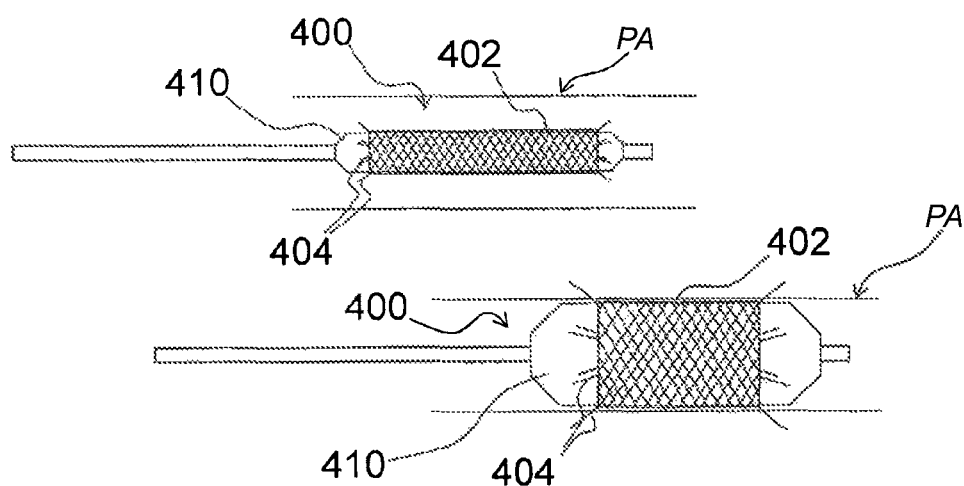
FIGS. 16A and 16B are schematic side-views, partially in section, of methods and apparatus for pulsed electric field neuromodulation comprising a stent having electrodes configured for intra-to-extravascular placement, according to one embodiment.

Referring now to FIGS. 16A and 16B, an alternative ITEV PEF 400 system is described comprising an expandable stent. The ITEV PEF system 400 comprises a stent 402 having extensions 404 configured to pierce the wall of a patient's vasculature upon expansion of the stent. The extensions 404 may be proximal and distal extensions that form longitudinally spaced bipolar electrode pairs. Additionally, the extensions 404 can be electrically coupled to the PEF generator 50 and utilized as extravascular electrodes for delivery of PEF therapy.

As seen in FIG. 16A, a stent 402 may be delivered to an intravascular treatment site, such as a site within pulmonary artery PA, in a reduced profile configuration. The stent 402 may, for example, be positioned on a delivery and deployment catheter, such as a balloon catheter 410, during advancement and deployment at the treatment site. The catheter 410 may (temporarily) electrically couple the stent to the PEF generator. As seen in FIG. 19B, when the stent 402 is properly positioned at the treatment site, it may be deployed to contact the vessel wall (e.g., via the deployment catheter) such that extensions 404 penetrate the wall of the vessel. This accordingly positions the extension electrodes extravascularly via an ITEV approach. PEF therapy then may proceed, and upon completion the catheter 410 may be collapsed and removed from the patient.

The system 400 facilitates repeat PEF therapy at a later time. For example, by temporarily electrically re-coupling the catheter 410 or some other electrical coupling element to the stent 402, the system 400 can repeat PEF therapy as desired. When utilized to achieve pulmonary denervation, such repeat therapy may, for example, be repeated upon evidence of re-innervation of the pulmonary arteries.

Referring now to FIG. 17, a portion of a pulmonary artery PA is illustrated in greater detail. More specifically, sympathetic nerves N typically run extending longitudinally along the lengthwise dimension L of a pulmonary artery PA, generally within the adventitia of the artery. For convenience purposes in this description, the term "pulmonary nerves" will be used generally to refer to any and all nerves such as those shown in FIG. 17 as well as any nerves that innervate any pulmonary vasculature. The pulmonary artery PA has smooth muscle cells SMC that surround the arterial circumference spiral around the angular axis $\theta$ of the artery, i.e., around the circumference of the artery. The smooth muscle cells of the pulmonary artery PA accordingly have a lengthwise or longer dimension extending transverse (i.e., non-parallel) to the lengthwise dimension of the pulmonary artery PA. The misalignment of the lengthwise dimensions of the pulmonary nerves and the smooth muscle cells is defined as "cellular misalignment."

Referring to FIGS. 18A and 18B, the cellular misalignment of the pulmonary nerves and the smooth muscle cells may be exploited to selectively affect pulmonary nerve cells with reduced effect on smooth muscle cells. More specifically, because larger cells require less energy to exceed the irreversibility threshold of electroporation, several embodiments of electrodes of the present invention are configured to align at least a portion of an electric field generated by the electrodes with or near the longer dimensions of the cells to be affected. In specific embodiments, the intravascular device has electrodes configured to create an electrical field aligned with or near the lengthwise dimension of the pulmonary artery PA to affect pulmonary nerves N. By aligning an electric field so that the field preferentially affects the lengthwise aspect of the cell rather than the diametric or radial aspect of the cell, lower field strengths may be used to necrose cells. As mentioned above, this is expected to reduce power consumption and mitigate effects on non-target cells in the electric field.

Similarly, the lengthwise or longer dimensions of tissues overlying or underlying the target nerve are orthogonal or otherwise off-axis (e.g., transverse) with respect to the longer dimensions of the nerve cells. Thus, in addition to aligning the PEF with the lengthwise or longer dimensions of the target cells, the PEF may propagate along the lateral or shorter dimensions of the non-target cells (i.e., such that the PEF propagates at least partially out of alignment with non-target smooth muscle cells SMC). Therefore, as seen in FIGS. 18A and 18B, applying a PEF with propagation lines Li generally aligned with the longitudinal dimension L of the pulmonary artery PA is expected to preferentially cause electroporation, electrofusion, denervation or other neuromodulation in cells of the target pulmonary nerves N without unduly affecting the non-target arterial smooth muscle cells SMC. The pulsed electric field may propagate in a single plane along the longitudinal axis of the pulmonary artery, or may propagate in the longitudinal direction along any angular segment θ through a range of 0-360 degrees.

Embodiments of the method shown in FIGS. 18A and 18B may have particular application with the intravascular methods and apparatus of the present invention. For instance, a PEF catheter placed within the pulmonary artery may propagate an electric field having a longitudinal portion that is aligned to run with the longitudinal dimension of the artery in the region of the pulmonary nerves N and the smooth muscle cell SMC of the vessel wall so that the wall of the artery remains at least substantially intact while the outer nerve cells are destroyed.

FIG. 19 shows one embodiment of an intravascular pulsed electric field apparatus 200 that includes one or more electrodes 212 configured to physically contact a target region within the pulmonary vasculature and deliver a pulsed electric field across a wall of the vasculature. The apparatus 200 is shown within a patient's pulmonary artery PA, but it can be positioned in other intravascular locations (e.g., a pulmonary vein). This embodiment of the apparatus 200 comprises an intravascular catheter 210 having a proximal section 211a, a distal section 211b, and a plurality of distal electrodes 212 at the distal section 211b. The proximal section 211a generally has an electrical connector to couple the catheter 210 to a pulse generator, and the distal section 211b in this embodiment has a helical configuration. The apparatus 200 is electrically coupled to a pulsed electric field generator 214 located proximal and external to the patient; the electrodes 212 are electrically coupled to the generator via catheter 210. The generator 214 may be utilized with any embodiment of the present invention described hereinafter for delivery of a PEF with desired field parameters. It should be understood that electrodes of embodiments described hereinafter may be connected to the generator, even if the generator is not explicitly shown or described with each variation.

The helical distal section 211b of catheter 210 is configured to appose the vessel wall and bring electrodes 212 into close proximity to extra-vascular neural structures. The pitch of the helix can be varied to provide a longer treatment zone, or to minimize circumferential overlap of adjacent treatments zones in order to reduce a risk of stenosis formation. This pitch change can be achieved by combining a plurality of catheters of different pitches to form catheter 210, or by adjusting the pitch of catheter 210 through the use of internal pull wires, adjusting mandrels inserted into the catheter, shaping sheaths placed over the catheter, or by any other suitable means for changing the pitch either in-situ or before introduction into the body.

The electrodes 212 along the length of the pitch can be individual electrodes, a common but segmented electrode, or a common and continuous electrode. A common and continuous electrode may, for example, comprise a conductive coil formed into or placed over the helical portion of catheter 210. A common but segmented electrode may, for example, be formed by providing a slotted tube fitted onto or into the helical portion of the catheter, or by electrically connecting a series of individual electrodes.

Individual electrodes or groups of electrodes 212 may be configured to provide a bipolar signal, or all or a subset of the electrodes may be used together in conjunction with a separate external patient ground for monopolar use (the ground pad may, for example, be placed on the patient's leg). Electrodes 212 may be dynamically assignable to facilitate monopolar and/or bipolar energy delivery between any of the electrodes and/or between any of the electrodes and an external ground.

Catheter 210 may be delivered to pulmonary artery PA in a low profile delivery configuration within sheath 150. Once positioned within the artery, the catheter may self-expand or may be expanded actively, e.g., via a pull wire or a balloon, into contact with an interior wall of the artery. A pulsed electric field then may be generated by the PEF generator 214, transferred through catheter 210 to electrodes 212, and delivered via the electrodes 212 across the wall of the artery. In many applications, the electrodes are aRPAnged so that the pulsed electric field is aligned with the longitudinal dimension of the artery to modulate the neural activity along the pulmonary nerves (e.g., denervation). This may be achieved, for example, via irreversible electroporation, electrofusion and/or inducement of apoptosis in the nerve cells.

Figure 20:
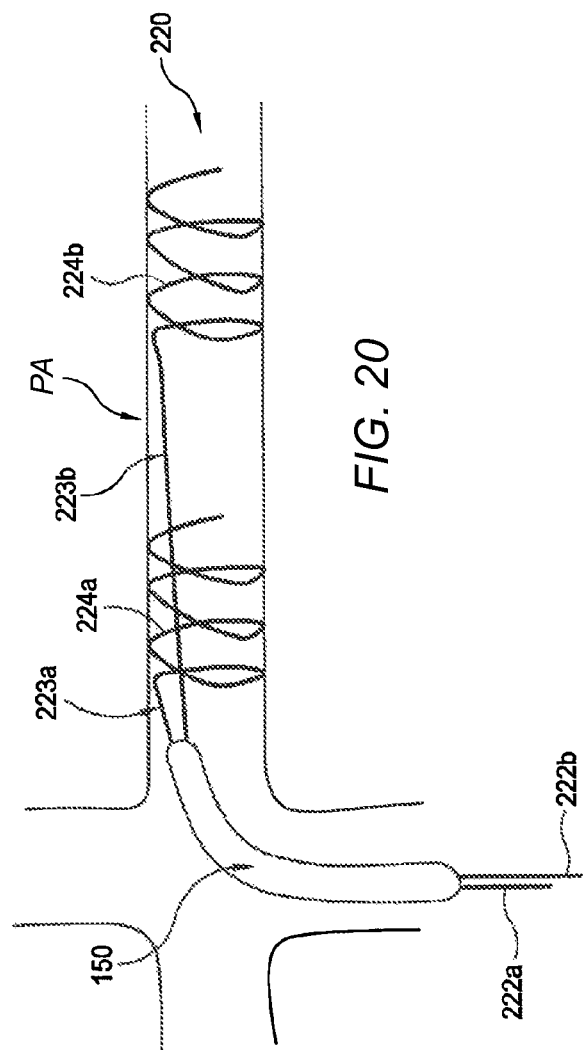
FIG. 20 is a schematic side-view, partially in section, of an intravascular device having a pair of expanding helical electrodes aRPAnged at a desired distance from one another, according to one embodiment.

Referring now to FIG. 20, an alternative embodiment of an apparatus 220 for neural modulation is illustrated. The apparatus 220 includes a pair of catheters 222a and 222b having expandable distal sections 223a and 223b with helical electrodes 224a and 224b, respectively. The helical electrodes 224a and 224b are spaced apart from each other by a desired distance within a patient's pulmonary vasculature. Electrodes 224a-b may be actuated in a bipolar fashion such that one electrode is an active electrode and the other is a return electrode. The distance between the electrodes may be altered as desired to change the field strength and/or the length of nerve segment modulated by the electrodes. The expandable helical electrodes may comprise shape-memory properties that facilitate self-expansion, e.g., after passage through sheath 150, or the electrodes may be actively expanded into contact with the vessel wall, e.g., via an inflatable balloon or via pull wires, etc. The catheters 222a-b preferably are electrically insulated in areas other than the distal helices of electrodes 224a-b.

Figure 21:
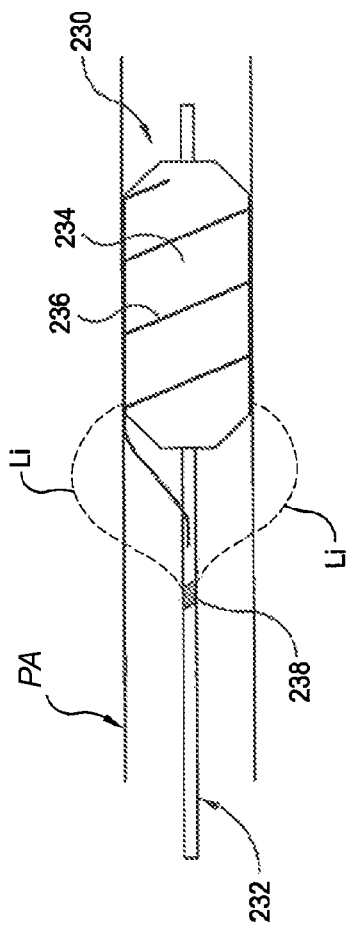
FIG. 21 is a schematic side-view, partially in section, of an intravascular device having a first electrode on an expandable balloon, and a second electrode on a catheter shaft, according to one embodiment.

FIG. 21 illustrates another alternative embodiment of an apparatus 230, comprising a balloon catheter 232 having expandable balloon 234, a helical electrode 236 aRPAnged about the balloon 234, and a shaft electrode 238 on the shaft of catheter 232. The shaft electrode 238 can be located proximal of expandable balloon 234 as shown, or the shaft electrode 238 can be located distal of the expandable balloon 234.

When the apparatus 230 is delivered to a target vessel, e.g., within pulmonary artery PA, the expandable balloon 234 and the helical electrode 236 are aRPAnged in a low profile delivery configuration. As seen in FIG. 21, once the apparatus has been positioned as desired, expandable balloon 234 may be inflated to drive the helical electrode 236 into physical contact with the wall of the vessel. In this embodiment, the shaft electrode 238 does not physically contact the vessel wall.

It is well known in the art of both traditional thermal RF energy delivery and of relatively non-thermal pulsed RF energy delivery that energy may be conducted to tissue to be treated from a short distance away from the tissue itself. Thus, "nerve contact" may include both physical contact of a system element with a nerve, as well as electrical contact alone without physical contact, or a combination of the two. A centering element optionally may be provided to place electrodes in a central region of the vessel. The centering element may comprise, for example, an expandable balloon, such as balloon 234 of apparatus 230, or an expandable basket as described hereinafter. One or more electrodes may be positioned on a central shaft of the centering element—either longitudinally aligned with the element or positioned on one or both sides of the element—as is shaft electrode 238 of apparatus 230. When utilizing a balloon catheter such as catheter 232, the inflated balloon may act as an insulator of increased impedance for directing a pulsed electric field along a desired electric flow path. As will be apparent, alternative insulators may be utilized.

As seen in FIG. 21, when the helical electrode 236 physically contacts the wall of pulmonary artery PA, the generator 214 may generate a PEF such that current passes between the helical electrode 236 and the shaft electrode 238 in a bipolar fashion. The PEF travels between the electrodes along lines Li that generally extend along the longitudinal dimension of the artery. The balloon 234 locally insulates and/or increases the impedance within the patient's vessel such that the PEF travels through the wall of the vessel between the helical and shaft electrodes. This focuses the energy to enhance denervation and/or other neuromodulation of the patient's pulmonary nerves, e.g., via irreversible electroporation.

FIG. 22 illustrates an apparatus 240 according to another embodiment. The apparatus 240 comprises a balloon catheter 242 having an expandable balloon 244 and a shaft electrode 246 located proximal of the expandable balloon 244. The apparatus 240 further comprises an expandable helical electrode 248 configured for delivery through a guidewire lumen 243 of the catheter 242. The helical electrode 248 shown in FIG. 22 is self-expanding.

As seen in FIG. 22, after positioning the catheter 242 in a target vessel (e.g. pulmonary artery PA), the balloon 244 is inflated until it contacts the wall of the vessel to hold the shaft electrode 246 at a desired location within the vessel and to insulate or increase the impedance of the interior of the vessel. The balloon 244 is generally configured to also center the shaft electrode 246 within the vessel or otherwise space the shaft electrode apart from the vessel wall by a desired distance. After inflating the balloon 244, the helical electrode 248 is pushed through lumen 243 until the helical electrode 248 extends beyond the catheter shaft; the electrode 248 then expands or otherwise moves into the helical configuration to physically contact the vessel wall. A bipolar pulsed electric field may then be delivered between the helical electrode 248 and the shaft electrode 246 along lines Li. For example, the helical electrode 248 may comprise the active electrode and the shaft electrode 246 may comprise the return electrode, or vice versa.

With reference now to FIGS. 23A and 23B, apparatus comprising an expandable basket 254 having a plurality of electrodes 256 that may be expanded into contact with the vessel wall is described. Apparatus 250 comprises catheter 252 having expandable distal basket 254 formed from a plurality of circumferential struts or members. A plurality of electrodes 256 are formed along the members of basket 254. Each member of the basket illustratively comprises a bipolar electrode pair configured to contact a wall of pulmonary artery PA or another desired blood vessel.

Basket 254 may be fabricated, for example, from a plurality of shape-memory wires or ribbons, such as Nitinol, spring steel or elgiloy wires or ribbons, that form basket members 253. When the basket members comprise ribbons, the ribbons may be moved such that a surface area contacting the vessel wall is increased. Basket members 253 are coupled to catheter 252 at proximal and distal connections 255a and 255b, respectively. In such a configuration, the basket may be collapsed for delivery within sheath 150, and may self-expand into contact with the wall of the artery upon removal from the sheath. Proximal and/or distal connection 255a and 255b optionally may be configured to translate along the shaft of catheter 252 for a specified or unspecified distance in order to facilitate expansion and collapse of the basket.

Basket 254 alternatively may be formed from a slotted and/or laser-cut hypotube. In such a configuration, catheter 252 may, for example, comprise inner and outer shafts that are moveable relative to one another. Distal connection 255b of basket 254 may be coupled to the inner shaft and proximal connection 255a of the basket may be coupled to the outer shaft. Basket 254 may be expanded from a collapsed delivery configuration to the deployed configuration of FIG. 8 by approximating the inner and outer shafts of catheter 252, thereby approximating the proximal and distal connections 255a and 255b of the basket and expanding the basket. Likewise, the basket may be collapsed by separating the inner and outer shafts of the catheter.

As seen in FIG. 23B, individual electrodes 256 may be aRPAnged along a basket strut or member 253. In one embodiment, the strut is formed from a conductive material coated with a dielectric material, and the electrodes 256 may be formed by removing regions of the dielectric coating. The insulation optionally may be removed only along a radially outer surface of the member such that electrodes 256 remain insulated on their radially interior surfaces; it is expected that this will direct the current flow outward into the vessel wall.

In addition, or as an alternative, to the fabrication technique of FIG. 23B, the electrodes may be affixed to the inside surface, outside surface or embedded within the struts or members of basket 254. The electrodes placed along each strut or member may comprise individual electrodes, a common but segmented electrode, or a common and continuous electrode. Individual electrodes or groups of electrodes may be configured to provide a bipolar signal, or all or a subset of the electrodes may be actuated together in conjunction with an external patient ground for monopolar use.

One advantage of having electrodes 256 contact the vessel wall, as shown in the embodiment of FIG. 23A, is that it may reduce the need for an insulating element, such as an expandable balloon, to achieve pulmonary denervation or other neuromodulation. However, such an insulating element may be provided and, for example, expanded within the basket. Furthermore, having the electrodes contact the wall may provide improved field geometry, i.e., may provide an electric field more aligned with the longitudinal axis of the vessel. Such contacting electrodes also may facilitate stimulation of the pulmonary nerves before, during or after neuromodulation to better position the catheter 252 before treatment or for monitoring the effectiveness of treatment.

In a variation of apparatus 250, electrodes 256 may be disposed along the central shaft of catheter 252, and basket 254 may simply center the electrodes within the vessel to facilitate more precise delivery of energy across the vessel wall. This configuration may be well suited to precise targeting of vascular or extra-vascular tissue, such as the pulmonary nerves surrounding the pulmonary artery. Correctly sizing the basket or other centering element to the artery provides a known distance between the centered electrodes and the arterial wall that may be utilized to direct and/or focus the electric field as desired. This configuration may be utilized in high-intensity focused ultrasound or microwave applications, but also may be adapted for use with any other energy modality as desired.

Figure 24A:
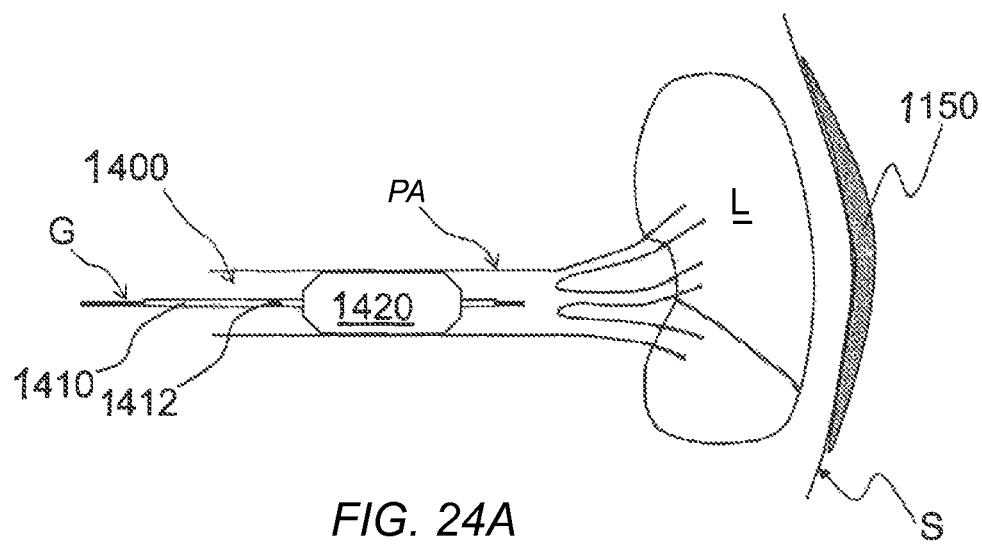
FIGS. 24A and 24B are schematic side views, partially in section, illustrating examples of monopolar intravascular methods and apparatus for pulmonary neuromodulation comprising centering elements, according to one embodiment.
Figure 24B:
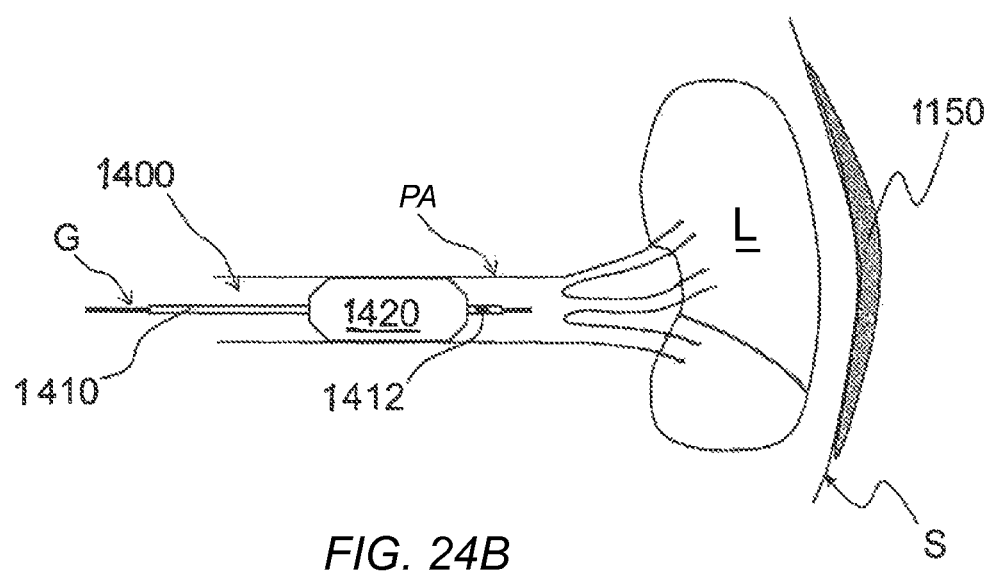

Referring now to FIGS. 24A and 24B, one embodiment of an intravascular monopolar PEF system 1400 is shown within a left pulmonary artery PA leading to a left lung L. (Like many figures herein, FIGS. 24A and 24B are not drawn to scale and are for illustrative purposes only. Furthermore, the left pulmonary artery PA is but one example of a target treatment location for system 1400.) In one embodiment, system 1400 optionally may comprise one or more centering elements for centering the monopolar electrode(s) within the patient's vasculature. The centering element(s) may be partially expanded such that they partially center the monopolar electrode(s) within the vessel, or may be fully expanded, as in FIGS. 24A and 24B, such that they substantially fully center the electrode(s) within the vessel. The centering elements 1420 may, for example, comprise inflatable balloons and/or expandable wire baskets or cages.

The centering element optionally may comprise an impedance-altering element configured to alter impedance within the patient's vasculature to better direct an applied electric field across the vessel wall to target neural fibers. When the centering element is a balloon, it may temporarily block blood flow and thereby alter the impedance within the patient's vessel. Additionally or alternatively, the centering element may comprise the monopolar electrode. In one embodiment, a balloon centering element comprises a conductive exterior and/or is fabricated from a conductive polymer and is used as the monopolar electrode.

In FIG. 24A, the PEF system 1400 comprises an expandable centering element 1420 coupled to the catheter 1410, which is shown advanced over a guidewire G. The element 1420 is configured for delivery and retrieval from a treatment site in a reduced profile delivery configuration, and for expansion at the treatment site to the deployed configuration of FIG. 24A. With the centering element in the fully expanded, deployed configuration of FIG. 24A, the monopolar electrode(s) 1412 are substantially centered within the vessel during the PEF therapy.

In the embodiment of FIG. 24A, the system 1400 comprises a unitary monopolar electrode 1412 positioned along the shaft of the catheter 1410 proximal of the centering element 1420. The centering element is accordingly positioned between the monopolar electrode 1412 and the ground pad 1150 (attached to the patient's skin S) in this embodiment. In the embodiment of FIG. 24B, the monopolar electrode 1412 is positioned distal of the centering element such that the centering element is not positioned between the monopolar electrode and the ground pad. Optionally, additional monopolar and/or bipolar electrodes may be provided with any of the embodiments of the system 1400 of FIGS. 24A and 24B at any desired position(s) along the catheter 1410. Furthermore, one or more electrodes may be coupled to the centering element(s) 1420 such that the electrodes contact the wall of the patient's vasculature during delivery of the PEF therapy.

It is expected that the monopolar PEF therapy, whether delivered extravascularly, intravascularly, intra-to-extravascularly or a combination thereof, may effectuate the following: irreversible electroporation or electrofusion; necrosis and/or inducement of apoptosis; alteration of gene expression; action potential blockade or attenuation; changes in cytokine up-regulation; and other conditions in target neural fibers. In some patients, when such neuromodulatory methods and apparatus are applied to pulmonary nerves and/or other neural fibers that contribute to pulmonary neural functions, applicants believe that the neuromodulatory effects induced by the neuromodulation might result in at least partial denervation of the patient's lung(s). This may result in increased pulmonary vascular diameter, decreasing pulmonary vascular resistance, reductions in pulmonary hypertension and/or reductions in systemic blood pressure. Furthermore, applicants believe that these or other changes might prevent or treat congestive heart failure, hypertension, myocardial infarction, pulmonary disease, other pulmonary system diseases, and/or other pulmonary or cardio-pulmonary anomalies for a period of months or even years (e.g., potentially up to six months or more).

The methods and apparatus described herein could be used to modulate efferent or afferent nerve signals, as well as combinations of efferent and afferent nerve signals. Neuromodulation in accordance with the present invention preferably is achieved without completely physically severing, i.e., without fully cutting, the target neural fibers. However, it should be understood that such neuromodulation may functionally sever the neural fibers even though the fibers may not be completely physically severed. Apparatus and methods described herein illustratively are configured for percutaneous use. Such percutaneous use may be endoluminal, laparoscopic, a combination thereof, etc.

The apparatus described herein additionally may be used to quantify the efficacy, extent or cell selectivity of PEF therapy to monitor and/or control the therapy. When a pulsed electric field initiates electroporation, the impedance of the electroporated tissue begins to decrease and the conductivity of the tissue begins to increase. If the electroporation is reversible, the tissue electrical parameters will return or approximate baseline values upon cessation of the PEF. However, if the electroporation is irreversible, the changes in tissue parameters will persist after termination of the PEF. These phenomena may be utilized to monitor both the onset and the effects of PEF therapy. For example, electroporation may be monitored directly using, for example, conductivity measurements or impedance measurements, such as Electrical Impedance Tomography ("EIT") and/or other electrical impedance/conductivity measurements like an electrical impedance or conductivity index. Such electroporation monitoring data optionally may be used in one or more feedback loops to control delivery of PEF therapy.

In order to collect the desired monitoring data, additional monitoring electrodes optionally may be provided in proximity to the monitored tissue. The distance between such monitoring electrodes preferably would be specified prior to therapy delivery and used to determine conductivity from impedance or conductance measurements. For the purposes of the present invention, the imaginary part of impedance may be ignored such that impedance is defined as voltage divided by current, while conductance may be defined as the inverse of impedance (i.e., current divided by voltage), and conductivity may be defined as conductance per unit distance.

Figure 25A:
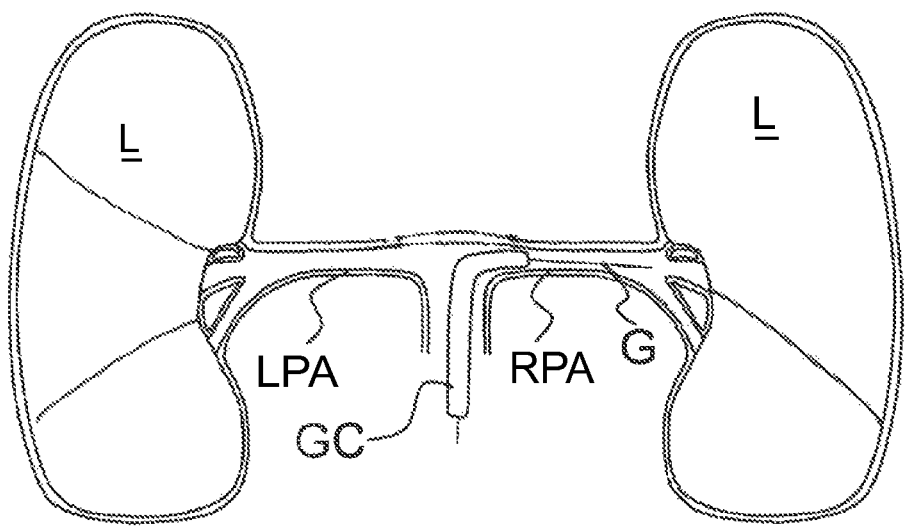
FIGS. 25A-25H are schematic side views, partially in section, illustrating methods of achieving bilateral pulmonary neuromodulation using apparatus according to one embodiment.
Figure 25B:
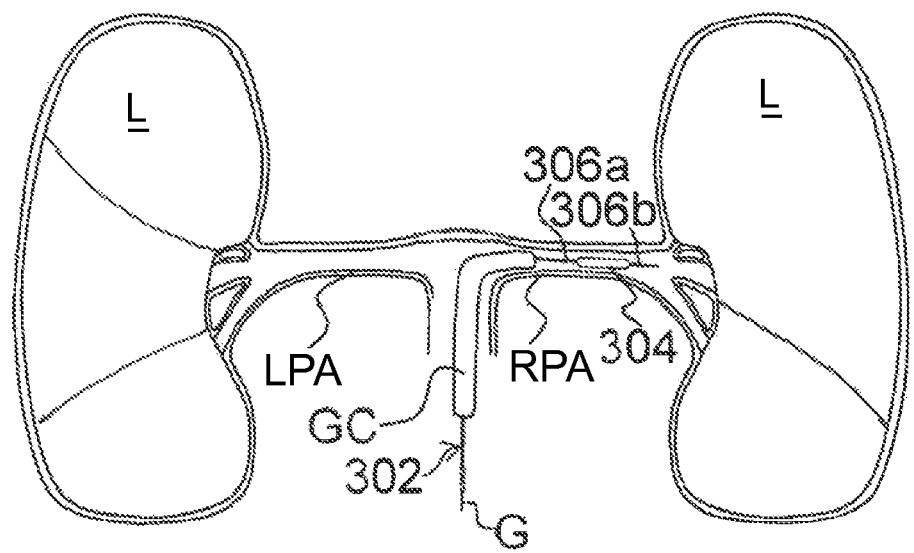
Figure 25C:
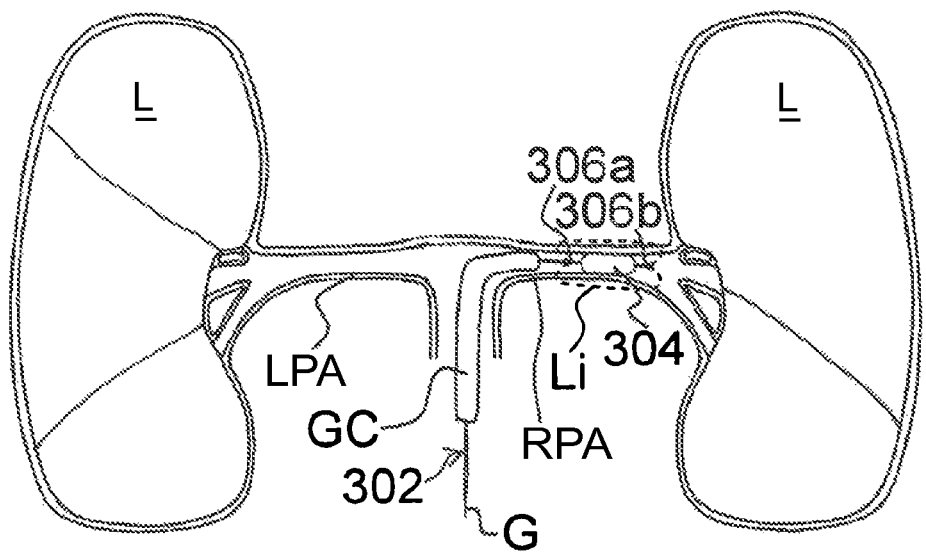
Figure 25D:
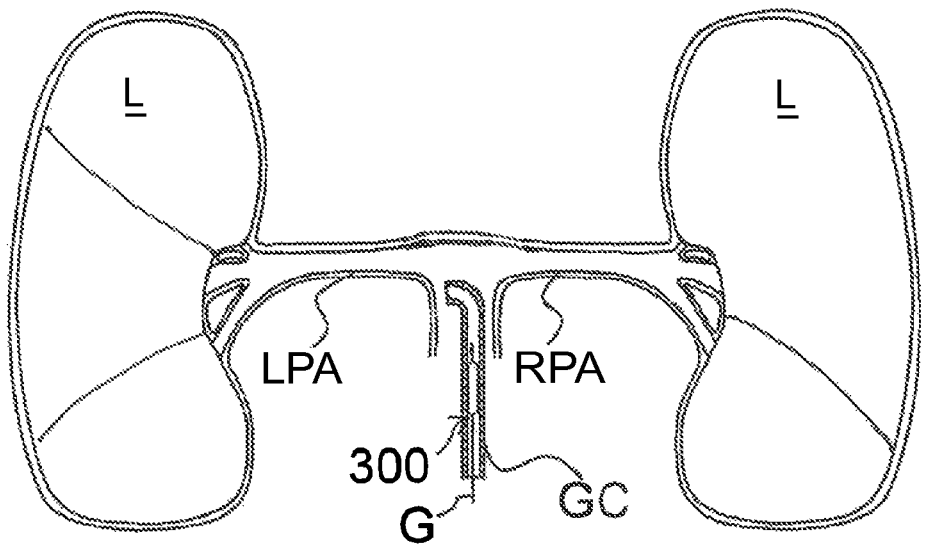
Figure 25E:
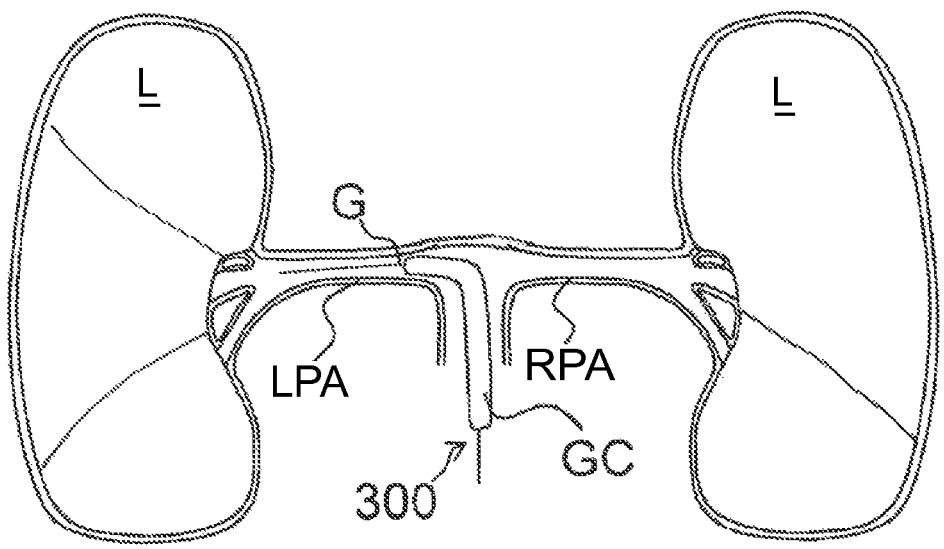

Referring now to FIGS. 25A-25H, a method for performing bilateral pulmonary neuromodulation is illustrated. As seen in FIGS. 25A and 25E, a guide catheter GC and a guidewire G may be advanced into position within, or in proximity to, either the patient's left pulmonary artery LPA or right pulmonary artery RPA. In FIG. 25A, the guidewire G illustratively has been positioned in the right pulmonary artery RPA, but in alternative embodiments, the order of bilateral pulmonary neuromodulation illustrated in FIGS. 25A-25H alternatively may be reversed. Additionally or alternatively, bilateral pulmonary neuromodulation may be performed concurrently on both right and left neural fibers that contribute to pulmonary function, as in FIGS. 26A and 26B, rather than sequentially, as in FIGS. 25A-25H.

With the guidewire G and the guide catheter GC positioned in the right pulmonary artery RPA, a catheter 302 of an apparatus 300 may be advanced over the guidewire G and through the guide catheter GC into position within the artery. As seen in FIG. 25B, an optional centering element 304 of the catheter 302 is in a reduced, delivery configuration during delivery of the catheter 302 to the pulmonary artery RPA. In FIG. 25C, once the catheter 302 is properly positioned for PEF therapy, the element 304 optionally may be expanded into contact with the vessel wall, and the guidewire G may be retracted from the treatment zone—for example, it may be removed from the patient or may be positioned more proximally within the patient's inferior vena cava.

Expansion of element 304 may center the electrodes 306a, 306b (referred to generally as 306) within the vessel and/or may alter impedance between the electrodes. With apparatus 300 positioned and deployed as desired, PEF therapy may be delivered in a bipolar fashion across the electrodes 306 to achieve pulmonary neuromodulation in neural fibers that contribute to right pulmonary function, e.g., to at least partially achieve pulmonary denervation of the right lung. As illustrated by propagation lines Li, the pulsed electric field may be aligned with a longitudinal dimension of the right pulmonary artery RPA and may pass across the vessel wall. The alignment and propagation path of the pulsed electric field is expected to preferentially modulate cells of the target pulmonary nerves without unduly affecting non-target arterial smooth muscle cells.

As seen in FIG. 25D, after completion of the PEF therapy, the element 304 may be collapsed back to the reduced delivery profile, and the catheter 302 may be retracted from the right pulmonary artery RPA, for example, to a position in the guide catheter GC within the patient's inferior vena cava. Likewise, the guide catheter GC may be retracted to a position within the patient's inferior vena cava. The retracted guide catheter GC may be repositioned, e.g., rotated, such that its distal outlet is generally aligned with the left pulmonary artery LPA. The guidewire G then may be re-advanced through the catheter 302 and the guide catheter GC to a position within the left pulmonary artery LPA, as shown in FIG. 25E. (In alternative embodiments, the order of advancement of the guidewire G and the guide catheter GC optionally may be reversed when accessing either pulmonary artery).

Figure 25F:
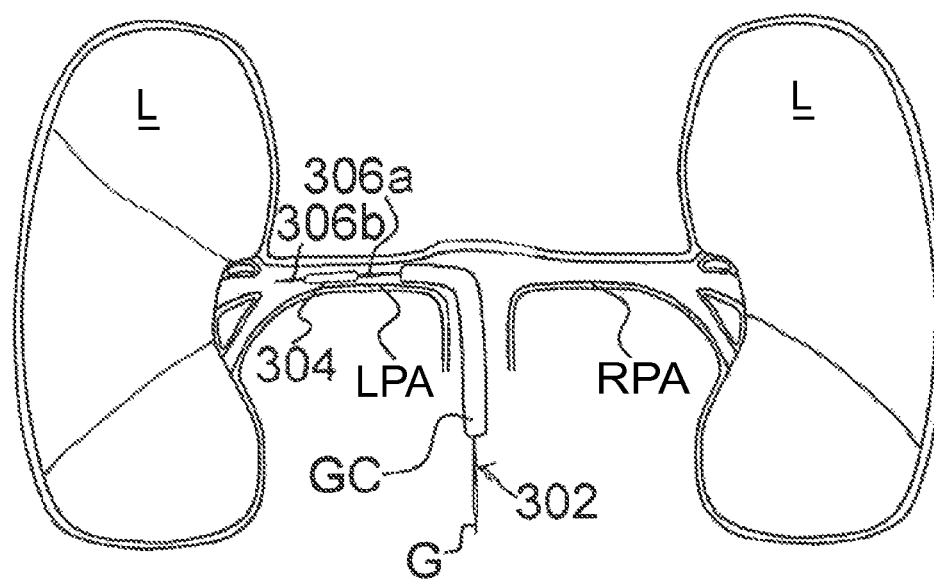
Figure 25G:
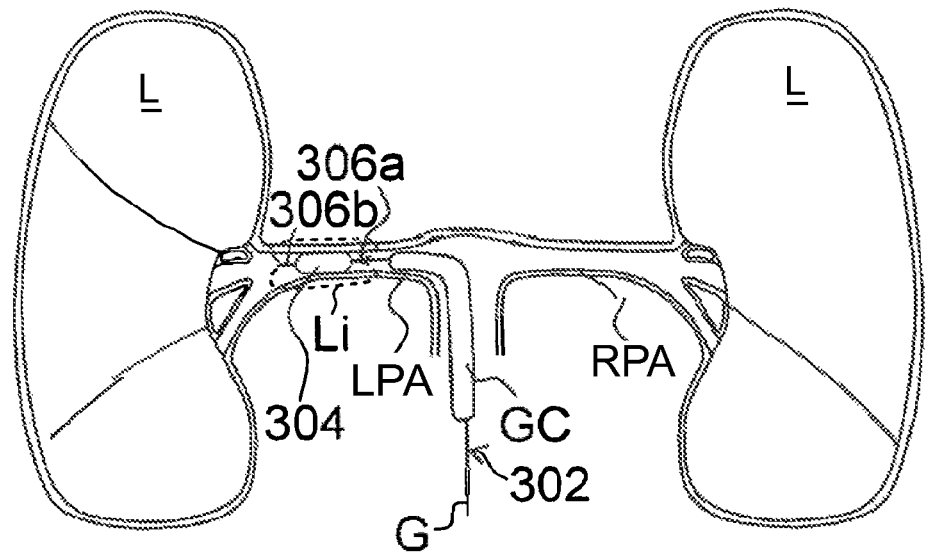
Figure 25H:
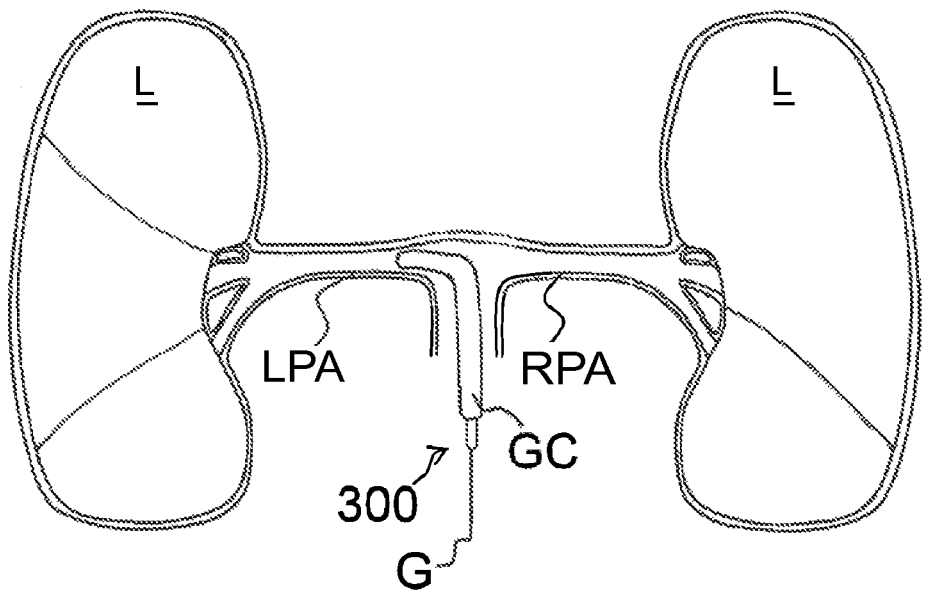

Next, the catheter 302 may be re-advanced over the guidewire G and through the guide catheter GC into position within the left pulmonary artery, as shown in FIG. 25F. In FIG. 25G, once the catheter is properly positioned for PEF therapy, the element 304 optionally may be expanded into contact with the vessel wall, and the guidewire G may be retracted to a position proximal of the treatment site. PEF therapy then may be delivered in a bipolar fashion across the electrodes 306, for example, along propagation lines Li, to achieve pulmonary neuromodulation in neural fibers that contribute to left pulmonary function, e.g., to at least partially achieve pulmonary denervation of the left lung. As seen in FIG. 25H, after completion of the bilateral PEF therapy, the element 304 may be collapsed back to the reduced delivery profile, and the catheter 302, as well as the guidewire G and the guide catheter GC, may be removed from the patient to complete the bilateral pulmonary neuromodulation procedure.

Figure 26A:
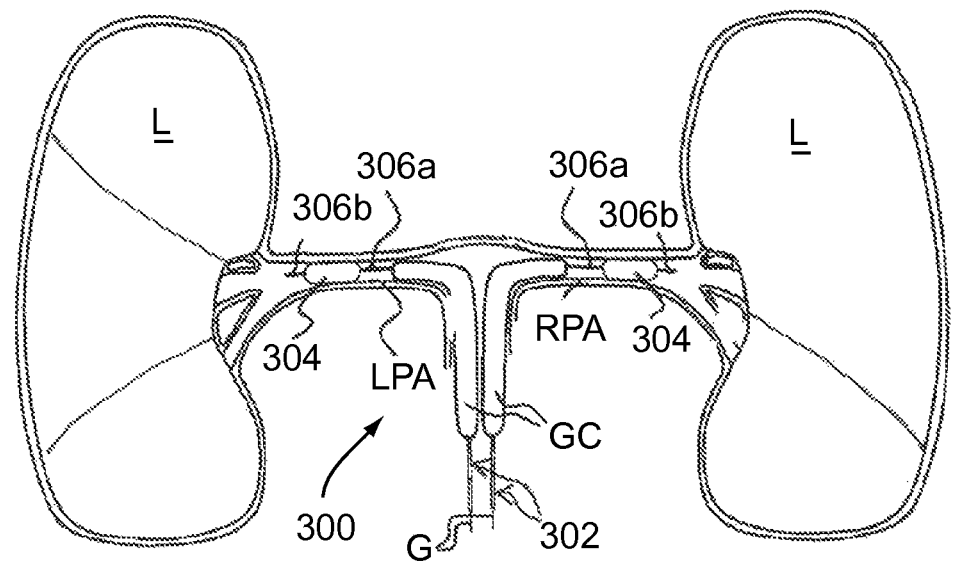
FIGS. 26A and 26B are schematic side views, partially in section, illustrating methods of achieving concurrent bilateral pulmonary neuromodulation apparatus according to one embodiment.
Figure 26B:
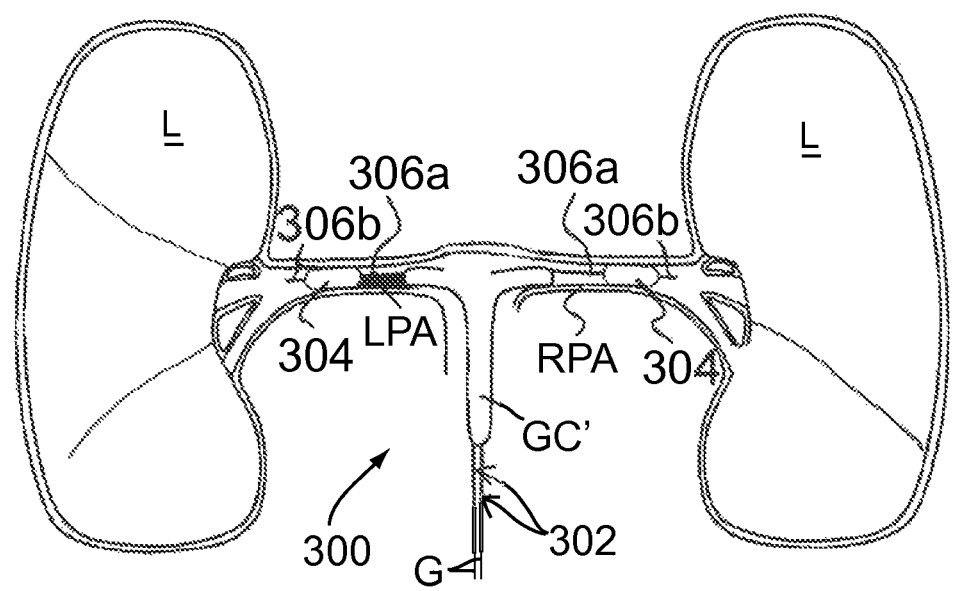

Referring now to FIGS. 26A and 26B, as discussed previously, bilateral pulmonary neuromodulation optionally may be performed concurrently on fibers that contribute to both right and left pulmonary function. FIGS. 26A and 26B illustrate embodiments of apparatus 300 for performing concurrent bilateral pulmonary neuromodulation. In the embodiment of FIG. 26A, apparatus 300 comprises dual PEF therapy catheters 302, as well as dual guidewires G and guide catheters GC. One catheter 302 is positioned within the right pulmonary artery RPA, and the other catheter 302 is positioned within the left pulmonary artery LPA. With catheters 302 positioned in both the right and left pulmonary arteries, PEF therapy may be delivered concurrently by the catheters 302 to achieve concurrent bilateral pulmonary neuromodulation, illustratively via an intravascular approach.

In one example, separate access sites in the patient's right and left femoral veins may be used for percutaneous delivery of the two catheters 302. Alternatively, both catheters 302 may be delivered through a single femoral access site, either through dual guide catheters or through a single guide catheter. FIG. 26B illustrates an example of apparatus 300 for concurrent bilateral pulmonary neuromodulation utilizing a single vascular access site. In the example of FIG. 26B, both catheters 302 are delivered through a custom bifurcated guide catheter GC' having a bifurcated distal region for concurrently delivering the catheters 302 to the right and left pulmonary arteries. Concurrent (or sequential) bilateral PEF therapy then may proceed.

Although illustrative variations of the present invention are described above, various changes and modifications may be made thereto without departing from the scope of the invention. For example, although some embodiments are primarily described for use in combination with pulsed electric fields, in alternative embodiments, any other electric field may be delivered as desired. As another example, method steps may be added or subtracted and/or an order of steps may be altered in various embodiments. In various embodiments, various alternative access routes, target tissues, treatment locations and amounts of treatment may be implemented. In some embodiments, for example, whole nerves may be destroyed, while in other embodiments, neurons may be down-regulated without being destroyed. Therefore, no one embodiment described above should be interpreted as limiting the scope of the invention as it is set forth in the claims.

We claim:

1. A method of performing a procedure to destroy nerve fibers of a nerve innervating a pulmonary artery to treat pulmonary hypertension in a patient, the method comprising:
    advancing a distal portion of a therapy delivery catheter to a target location in the pulmonary artery of the patient;
    changing a shape of the distal portion of the catheter from a first configuration to a second configuration to cause the distal portion to contact an inner wall of the pulmonary artery at the target location;
    delivering a therapy from at least one therapy delivery member disposed along the distal portion of the catheter to destroy the nerve fibers along a length of the nerve to treat the pulmonary hypertension in the patient; and removing the catheter from the pulmonary artery and from the patient at the end of the procedure.

2. A method as in claim 1, further comprising, before removing the catheter, changing the shape of the distal portion from the second configuration to the first configuration.

3. A method as in claim 1, wherein the nerve comprises a sympathetic nerve.

4. A method as in claim 1, wherein changing the shape of the distal portion from the first configuration to the second configuration comprises inflating an inflatable balloon.

5. A method as in claim 1, wherein changing the shape of the distal portion from the first configuration to the second configuration comprises releasing a shape-memory portion of the catheter from a constraint to allow it to assume a default configuration.

6. A method as in claim 1, wherein the at least one therapy delivery member comprises at least one energy delivery member, and wherein delivering the therapy comprises delivering a form of energy selected from the group consisting of radiofrequency, ultrasound, microwave, light, heat, cold, radiation, phototherapy, magnetic, electrical, electromagnetic, cryotherapy, plasma, mechanical, chemical, kinetic, potential, nuclear, elastic and hydrodynamic energy.

7. A method as in claim 1, wherein the at least one therapy delivery member comprises at least one substance delivery member, and wherein delivering the therapy comprises delivering at least one substance via the at least one substance delivery member.

8. A method as in claim 1, wherein delivering the therapy from the at least one therapy delivery member comprises delivering the therapy from multiple therapy delivery members disposed along a length of the distal portion and around a circumference of the distal portion.

9. A method as in claim 1, wherein, after the catheter is removed, no implant is left behind in the pulmonary artery.

10. A method of performing a procedure to treat pulmonary hypertension by reducing pulmonary vascular resistance in a patient, the method comprising:

advancing an energy delivery portion of a catheter to a target location in a pulmonary artery;

changing a shape of the energy delivery portion from a first configuration to a second configuration to contact an inner wall of the pulmonary artery at the target location with multiple, circumferential energy delivery members disposed at separated locations along a length of the energy delivery portion;

delivering energy from the energy delivery members to destroy nerve fibers of a sympathetic nerve that innervates the pulmonary artery to reduce the pulmonary vascular resistance in the patient and thus treat pulmonary hypertension; and removing the catheter from the pulmonary artery at the end of the procedure.

11. A method as in claim 10, further comprising, before removing the catheter, changing the shape of the energy delivery portion from the second configuration to the first configuration.

12. A method as in claim 10, wherein changing the shape of the energy delivery portion from the first configuration to the second configuration comprises inflating an inflatable balloon.

13. A method as in claim 10, wherein changing the shape of the energy delivery portion from the first configuration to the second configuration comprises releasing a shape-memory portion of the catheter from a constraint to allow it to assume a default configuration.

14. A method as in claim 10, wherein delivering energy from the energy delivery members comprises delivering a form of energy selected from the group consisting of radiofrequency, ultrasound, microwave, light, heat, cold, radiation, phototherapy, magnetic, electrical, electromagnetic, cryotherapy, plasma, mechanical, chemical, kinetic, potential, nuclear, elastic and hydrodynamic energy.

15. A method as in claim 10, wherein, after the catheter is removed, no implant is left behind in the pulmonary artery.

* * * * *